(12) United States Patent
Yamamoto et al.

(10) Patent No.: US 9,018,323 B2
(45) Date of Patent: Apr. 28, 2015

(54) POLYMER DERIVATIVE OF CYTIDINE METABOLIC ANTAGONIST

(75) Inventors: Keiichirou Yamamoto, Tokyo (JP); Manami Okazaki, Tokyo (JP); Dai Kawamura, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 182 days.

(21) Appl. No.: 13/884,413

(22) PCT Filed: Nov. 16, 2011

(86) PCT No.: PCT/JP2011/076373
§ 371 (c)(1),
(2), (4) Date: Jun. 5, 2013

(87) PCT Pub. No.: WO2012/067138
PCT Pub. Date: May 24, 2012

(65) Prior Publication Data
US 2013/0331517 A1  Dec. 12, 2013

(30) Foreign Application Priority Data

Nov. 17, 2010 (JP) ................................ 2010-257013

(51) Int. Cl.
| | | |
|---|---|---|
| C08G 81/00 | (2006.01) | |
| A61K 31/513 | (2006.01) | |
| C07D 407/04 | (2006.01) | |
| C08G 69/40 | (2006.01) | |
| C08G 69/48 | (2006.01) | |
| A61K 31/77 | (2006.01) | |
| A61K 31/785 | (2006.01) | |
| A61K 47/48 | (2006.01) | |
| C08G 85/00 | (2006.01) | |

(52) U.S. Cl.
CPC .............. *C08G 81/00* (2013.01); *A61K 31/513* (2013.01); *C07D 407/04* (2013.01); *C08G 69/40* (2013.01); *C08G 69/48* (2013.01); *A61K 31/77* (2013.01); *A61K 31/785* (2013.01); *A61K 47/48215* (2013.01); *A61K 47/48315* (2013.01); *C08G 85/004* (2013.01)

(58) Field of Classification Search
CPC .... C07D 407/04; A61K 31/513; C08G 69/48; C08G 69/40
See application file for complete search history.

(56) References Cited

U.S. PATENT DOCUMENTS

| | | | |
|---|---|---|---|
| 3,979,449 A | 9/1976 | Hirsbrunner et al. | |
| 4,734,512 A | 3/1988 | Kaneko et al. | |
| 4,892,733 A | 1/1990 | Bichon et al. | |
| 5,037,883 A | 8/1991 | Kopecek et al. | |
| 5,182,203 A | 1/1993 | Ebersole et al. | |
| 5,412,072 A | 5/1995 | Sakurai et al. | |
| 5,438,072 A | 8/1995 | Bobee et al. | |
| 5,510,103 A | 4/1996 | Yokoyama et al. | |
| 5,552,517 A | 9/1996 | Martin | |
| 5,571,889 A | 11/1996 | Katoh et al. | |
| 5,614,549 A | 3/1997 | Greenwald et al. | |
| 5,639,832 A | 6/1997 | Kroner et al. | |
| 5,693,751 A | 12/1997 | Sakurai et al. | |
| 5,877,205 A | 3/1999 | Andersson | |
| 5,985,548 A | 11/1999 | Collier et al. | |
| 6,025,385 A | 2/2000 | Shimizu et al. | |
| 6,153,655 A | 11/2000 | Martinez et al. | |
| 6,262,107 B1 | 7/2001 | Li et al. | |
| 6,322,817 B1 | 11/2001 | Maitra et al. | |
| 6,376,470 B1 | 4/2002 | Greenwald et al. | |
| 6,410,731 B2 | 6/2002 | Curran et al. | |
| 6,458,347 B1 | 10/2002 | Sugawara et al. | |
| 6,573,284 B1 | 6/2003 | Riley et al. | |
| 6,596,757 B1 | 7/2003 | Chari et al. | |

(Continued)

FOREIGN PATENT DOCUMENTS

| | | |
|---|---|---|
| CA | 2383240 A1 | 3/2001 |
| CA | 2334615 A1 | 8/2001 |

(Continued)

OTHER PUBLICATIONS

Office Action dated Apr. 17, 2009 in co-pending U.S. Appl. No. 10/548,998.

(Continued)

*Primary Examiner* — Joseph Kosack
*Assistant Examiner* — Matthew Coughlin
(74) *Attorney, Agent, or Firm* — Nields, Lemack & Frame, LLC

(57) ABSTRACT

[Problem]To provide a novel polymer derivative of a cytidine metabolic antagonist which allows release of a medicament irrespective of enzymes of the living body and is expected to have high therapeutic effects. [Solution]

The polymer derivative of a cytidine metabolic antagonist in which a substituent represented by the general formula (I) or the general formula (II) [wherein $R^7$ and $R^8$ each independently represent a hydrogen atom or an optionally substituted (C1-C6)alkyl group, $R^6$ represents a hydrogen atom, an optionally substituted (C1-C40)alkyl group, an optionally substituted (C1-C40)aralkyl group, an optionally substituted aromatic group, an amino acid residue in which the carboxy group is protected, or an optionally substituted sugar residue, CX—CY represents CH—CH or C=C (double bond), and A represents the residue of the cytidine metabolic antagonist except the amino group at the position 4] is bonded to the side-chain carboxy group of a block copolymer of a polyethylene-glycol structural moiety and a polymer having 10 or more carboxy groups.

10 Claims, 1 Drawing Sheet

(56) References Cited

U.S. PATENT DOCUMENTS

| | | |
|---|---|---|
| 6,713,454 B1 | 3/2004 | Ekwuribe et al. |
| 6,720,304 B1 | 4/2004 | Sinn et al. |
| 6,720,306 B2 | 4/2004 | Greenwald et al. |
| 6,858,582 B2 | 2/2005 | Yatvin et al. |
| 7,138,490 B2 | 11/2006 | Nakanishi et al. |
| 7,176,185 B2 | 2/2007 | Hilfinger et al. |
| 7,495,099 B2 | 2/2009 | Kitagawa et al. |
| 7,700,709 B2 | 4/2010 | Masuda et al. |
| 7,820,759 B2 | 10/2010 | Shimizu et al. |
| 8,188,222 B2 | 5/2012 | Yamamoto et al. |
| 8,323,669 B2 | 12/2012 | Kitagawa et al. |
| 8,334,364 B2 | 12/2012 | Yamamoto et al. |
| 8,703,878 B2 | 4/2014 | Kitagawa et al. |
| 8,808,749 B2 | 8/2014 | Kitagawa et al. |
| 8,920,788 B2 | 12/2014 | Kitagawa et al. |
| 8,940,332 B2 | 1/2015 | Kitagawa et al. |
| 2001/0003779 A1 | 6/2001 | Curran et al. |
| 2001/0014354 A1 | 8/2001 | Yokoyama et al. |
| 2001/0041189 A1 | 11/2001 | Xu |
| 2002/0009426 A1 | 1/2002 | Greenwald et al. |
| 2002/0016285 A1 | 2/2002 | Bhatt et al. |
| 2002/0099013 A1 | 7/2002 | Piccariello et al. |
| 2002/0119951 A1 | 8/2002 | Seyedi et al. |
| 2002/0161062 A1 | 10/2002 | Biermann et al. |
| 2002/0183259 A1 | 12/2002 | Choe et al. |
| 2003/0032593 A1 | 2/2003 | Wender et al. |
| 2003/0054977 A1 | 3/2003 | Kumar et al. |
| 2003/0149003 A1 | 8/2003 | Chaplin et al. |
| 2005/0054026 A1 | 3/2005 | Atsushi et al. |
| 2005/0119193 A1 | 6/2005 | Motoyama |
| 2005/0147617 A1 | 7/2005 | Ji et al. |
| 2005/0171036 A1 | 8/2005 | Arakawa et al. |
| 2006/0009622 A1 | 1/2006 | Fuselier et al. |
| 2006/0057219 A1 | 3/2006 | Nagasaki et al. |
| 2006/0067910 A1 | 3/2006 | Kitagawa et al. |
| 2006/0099265 A1 | 5/2006 | Shimizu et al. |
| 2006/0233883 A1 | 10/2006 | Ishihara et al. |
| 2006/0258569 A1 | 11/2006 | McTavish |
| 2007/0004674 A1 | 1/2007 | Shiotsu et al. |
| 2007/0196497 A1 | 8/2007 | Pouliquen et al. |
| 2008/0113028 A1 | 5/2008 | Shimizu et al. |
| 2008/0145432 A1 | 6/2008 | Kakizawa et al. |
| 2008/0221062 A1 | 9/2008 | Miyamoto et al. |
| 2008/0269218 A1 | 10/2008 | Kuramochi et al. |
| 2008/0280937 A1 | 11/2008 | Leamon et al. |
| 2009/0012252 A1 | 1/2009 | Masuda et al. |
| 2009/0156742 A1 | 6/2009 | Shimizu et al. |
| 2009/0162313 A1 | 6/2009 | Kitagawa et al. |
| 2009/0239782 A1 | 9/2009 | Nakamura et al. |
| 2009/0275732 A1 | 11/2009 | Hirotsu et al. |
| 2009/0281300 A1 | 11/2009 | Yamamoto et al. |
| 2010/0004403 A1 | 1/2010 | Kitagawa et al. |
| 2010/0029849 A1* | 2/2010 | Yamamoto et al. .......... 525/54.2 |
| 2010/0234537 A1 | 9/2010 | Kitagawa et al. |
| 2010/0292414 A1 | 11/2010 | Kitagawa et al. |
| 2011/0136990 A1 | 6/2011 | Harada et al. |
| 2011/0201754 A1 | 8/2011 | Kitagawa et al. |
| 2011/0294980 A1 | 12/2011 | Nakanishi et al. |
| 2012/0116051 A1 | 5/2012 | Kitagawa et al. |
| 2014/0024703 A1 | 1/2014 | Shimizu et al. |
| 2014/0142167 A1 | 5/2014 | Shimizu et al. |
| 2014/0288244 A1 | 9/2014 | Yamamoto et al. |
| 2015/0011715 A1 | 1/2015 | Nakamura et al. |

FOREIGN PATENT DOCUMENTS

| | | |
|---|---|---|
| CN | 1307866 A | 8/2001 |
| CN | 1708540 A | 12/2005 |
| CN | 1800238 A | 7/2006 |
| EP | 0397307 A2 | 11/1990 |
| EP | 0583955 A2 | 2/1994 |
| EP | 0757049 A1 | 2/1997 |
| EP | 1127570 A2 | 8/2001 |
| EP | 1580216 A1 | 9/2005 |
| EP | 1857446 A1 | 11/2007 |
| JP | 61-243026 A | 10/1986 |
| JP | 62-96088 A | 5/1987 |
| JP | 62-145093 A | 6/1987 |
| JP | 63-10789 A | 1/1988 |
| JP | 63-23884 A | 2/1988 |
| JP | 63-502037 A | 8/1988 |
| JP | 64-61422 A | 3/1989 |
| JP | 64-61423 A | 3/1989 |
| JP | 2-300133 A | 12/1990 |
| JP | 5-955 A | 1/1993 |
| JP | 5-117385 A | 5/1993 |
| JP | 6-107565 A | 4/1994 |
| JP | 6-206815 A | 7/1994 |
| JP | 6-206830 A | 7/1994 |
| JP | 6-206832 A | 7/1994 |
| JP | 6-329085 A | 11/1994 |
| JP | 8-48766 A | 2/1996 |
| JP | 8-503689 H | 4/1996 |
| JP | 8-507558 A | 8/1996 |
| JP | 8-310970 A | 11/1996 |
| JP | 2694923 B2 | 12/1997 |
| JP | 10-513187 H | 12/1998 |
| JP | 11-335267 A | 12/1999 |
| JP | 2000-515132 A | 11/2000 |
| JP | 2000-516948 A | 12/2000 |
| JP | 2000-517304 A | 12/2000 |
| JP | 2001-226294 A | 8/2001 |
| JP | 2002-69184 A | 3/2002 |
| JP | 2002-508400 A | 3/2002 |
| JP | 3268913 B2 | 3/2002 |
| JP | 2002-512265 A | 4/2002 |
| JP | 3310000 B2 | 7/2002 |
| JP | 2003-509385 A | 3/2003 |
| JP | 2003-509386 A | 3/2003 |
| JP | 2003-511349 A | 3/2003 |
| JP | 2003-511423 A | 3/2003 |
| JP | 2003-524028 A | 8/2003 |
| JP | 2003-525238 A | 8/2003 |
| JP | 2003-527443 A | 9/2003 |
| JP | 2003-342167 A | 12/2003 |
| JP | 2003-342168 A | 12/2003 |
| JP | 2003-342269 A | 12/2003 |
| JP | 2004-530736 A | 10/2004 |
| JP | 2004-532289 A | 10/2004 |
| JP | 2005-507912 A | 3/2005 |
| JP | 2005-508832 A | 4/2005 |
| JP | 2005-517675 A | 6/2005 |
| JP | 2005-519122 A | 6/2005 |
| JP | 2005-533026 A | 11/2005 |
| JP | 2006-510627 A | 3/2006 |
| JP | 2006-511571 A | 4/2006 |
| JP | 2006-517572 A | 7/2006 |
| JP | 2006-521367 A | 9/2006 |
| JP | 2006-524673 A | 11/2006 |
| JP | 2007-511586 A | 5/2007 |
| JP | 2007-191643 A | 8/2007 |
| WO | 93/24476 A1 | 12/1993 |
| WO | 96/23794 A1 | 8/1996 |
| WO | 97/38727 A1 | 10/1997 |
| WO | 98/02426 A1 | 1/1998 |
| WO | 98/07713 A | 2/1998 |
| WO | 98/08489 A1 | 3/1998 |
| WO | 99/30727 A1 | 6/1999 |
| WO | 99/53951 A1 | 10/1999 |
| WO | 01/19361 A2 | 3/2001 |
| WO | 01/19406 A2 | 3/2001 |
| WO | 01/19407 A2 | 3/2001 |
| WO | 01/26693 A2 | 4/2001 |
| WO | 01/64198 A2 | 9/2001 |
| WO | 01/70275 A2 | 9/2001 |
| WO | 01/92584 A1 | 12/2001 |
| WO | 02/06279 A1 | 1/2002 |
| WO | 02/065986 A2 | 8/2002 |
| WO | 02/065988 A2 | 8/2002 |
| WO | 02/066066 A1 | 8/2002 |
| WO | 03/000771 A1 | 1/2003 |
| WO | 03/035008 A2 | 5/2003 |
| WO | 03/055860 A1 | 7/2003 |

(56) References Cited

FOREIGN PATENT DOCUMENTS

| WO | 2004/039869 A1 | 5/2004 |
|---|---|---|
| WO | 2004/050087 A1 | 6/2004 |
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |
| WO | 2010/131675 A1 | 11/2010 |

OTHER PUBLICATIONS

Office Action dated Jul. 10, 2009 in co-pending U.S. Appl. No. 10/548,998.
Final Rejection dated Mar. 4, 2010 in co-pending U.S. Appl. No. 10/548,998.
Office Action dated Aug. 24, 2010 in co-pending U.S. Appl. No. 11/662,834.
Office Action dated Nov. 12, 2010 in co-pending U.S. Appl. No. 11/662,834.
Final Rejection dated Jun. 8, 2011 in co-pending U.S. Appl. No. 11/662,834.
Office Action mailed Dec. 15, 2011 in co-pending U.S. Appl. No. 11/662,834.
Final Rejection mailed Aug. 21, 2012 in co-pending U.S. Appl. No. 11/662,834.
Office Action dated Sep. 9, 2011 in co-pending U.S. Appl. No. 12/226,962.
Final Rejection mailed Feb. 16, 2012 in co-pending U.S. Appl. No. 12/226,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Office Action mailed Apr. 18, 2013 in co-pending U.S. Appl. No. 12/311,086.
Office Action mailed Apr. 25, 2012 in co-pending U.S. Appl. No. 12/678,620.
Final Rejection mailed Oct. 17, 2012 in co-pending U.S. Appl. No. 12/678,620.
Office Action—Restriction—mailed Apr. 27, 2012 in co-pending U.S. Appl. No. 12/922,747.
Office Action mailed Jul. 30, 2012 in co-pending U.S. Appl. No. 12/922,747.
Final Rejection mailed Mar. 5, 2013 in co-pending U.S. Appl. No. 12/922,747.
Office Action—Restriction—mailed Jul. 11, 2012 in co-pending U.S. Appl. No. 12/991,041.
Office Action mailed Aug. 22, 2012 in co-pending U.S. Appl. No. 12/991,041.
Final Rejection mailed Mar. 28, 2013 in co-pending U.S. Appl. No. 12/991,041.
Office Action—Restriction—mailed Jan. 29, 2013 in co-pending U.S. Appl. No. 13/319,175.
Office Action mailed Jun. 12, 2013 in co-pending U.S. Appl. No. 13/319,175.
Course for Universities, Third Edition, Revised and supplemented, "Visshaja Shkola" Publishing House, 1981, 656 pages, see p. 265, "High-Molecular Weight Compounds", SHUR.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview—Amphiphilic Block Copolymers for Drug Delivery", Adams, et al.
Chemistry and Biology, vol. 11, 787-797, Jun. 2004, "Targeting Wide-Range Oncogenic Transformation via PU24FCI, a Specific Inhibitor of Tumor Hsp90", Vilenchik, et al.
Trends in Molecular Medicine, vol. 8, No. 4, (Supp.) 2002, p. S55-61, "Hsp90 Inhibitors as Novel Cancer Chemotherapeutic Agents", Neckers, et al.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, Jan. 25-30, 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.
J.of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Journal of Peptide Science, vol. 3 (1997), 141-144, "Evaluation of Carbodiimides Using a Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.
Registry Entry for Registry No. 7689-03-4, which entered STN on Nov. 16, 1984, 3 pages.
Merriam Webster Online Dictionary entry for "Derivative", (http://www.merriam-webster.com/dictionary/derivative), last accessed Feb. 9, 2011, 3 pages.
Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.

(56) References Cited

OTHER PUBLICATIONS

Pharmaceutical Research, V. 17, No. 5 (2000) pp. 607-611, "Methotrexate Esters of Poly(EthyleneOxide)-Block-Poly (2-Hydroxyethyl-L-Aspartamide). Part I: Effects of the Level of Methotrexate Conjugation on the Stability of Micelles and on Drug Release", Li, et al.
Journal of Controlled Release, 2001, V. 74, No. 1-3, pp. 295-302, paragraph of "2. Structure of NK911", "Development of the polymer micelle carrier system for doxorubicin", Nakanishi, et al.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Advanced Drug Delivery Reviews, vol. 55, No. 2, Feb. 2003, pp. 217-250, "Effective drug delivery by PEGylated drug conjugates", Greenwald, et al.
Chinese Communication, with English translation, mailed Dec. 31, 2013 in co-pending Chinese patent application No. CN 200980110087.5.
International Search Report dated Dec. 24, 2003 in international patent application No. PCT/JP03/13838.
Taiwanese Communication dated Nov. 30, 2006 in international patent application No. TW092130275.
Russian Communication dated Apr. 20, 2007 in international patent application No. RU2005116309.
European Communication dated Sep. 25, 2008 in international patent application No. EP03769949.3.
International Search Report dated May 11, 2004 in co-pending international patent application No. PCT/JP2004/003647.
Chinese Communicaton dated Oct. 20, 2006 in co-pending international patent application No. CN200480007329.5.
Russian Communication dated Jun. 27, 2007 in co-pending international patent application No. RU2005132309/04.
European Communication dated Feb. 17, 2009 in co-pending international patent application No. EP04721673.4.
Chinese Communication, with English translation, dated Apr. 17, 2009 in co-pending international patent application No. CN200480007329.5.
European Communication dated Jun. 5, 2009 in co-pending international patent application No. EP04721673.4.
Korean Communication dated Nov. 8, 2010 in co-pending international patent application No. 10-2005-7017245.
International Search Report dated Nov. 15, 2005 in co-pending international patent application No. PCT/JP2005/017127.
Taiwanese Communication dated Jul. 22, 2011 in co-pending Taiwanese patent application No. 094132581.
European Communication, dated Oct. 28, 2011 in co-pending European Patent Application No. EP 05783310.5.
Taiwanese Communication, with English translation, dated Dec. 14, 2011 in co-pending Taiwanese Application No. 094132581.
International Search Report dated Jul. 25, 2006 in international patent application No. PCT/JP2006/308826.
International Search Report dated May 15, 2007 in co-pending international patent application No. PCT/JP2007/055809.
International Search Report dated Aug. 21, 2007 in co-pending international patent application No. PCT/JP2007/060026.
European Communication dated Oct. 23, 2009 in co-pending international patent application No. EP07743461.1.
Chinese Communication, with English translation, dated Aug. 11, 2010 in co-pending international patent application No. CN2007800177809.
Russian Communication, with English translation, mailed May 16, 2011 in co-pending international patent application No. RU2008149932/04.
Chinese Communication, with English translation, dated Sep. 23, 2011 in co-pending Chinese patent application No. 2007800177809.
Australian Communication, dated Oct. 28, 2011 in co-pending Australian Patent Application No. 2007252678.
International Search Report dated Oct. 16, 2007 in co-pending international patent application No. PCT/JP2007/063990.
Chinese Communication dated Nov. 10, 2010 in co-pending international patent application No. CN 200780027210.8.
International Search Report dated Jan. 8, 2008 in co-pending international patent application No. PCT/JP2007/068841.
Japanese Communication, with English translation, mailed Mar. 26, 2013 in co-pending Japanese Patent Application No. 2008-537500.
International Search Report dated Jan. 29, 2008 in co-pending international patent application No. PCT/JP2007/071532.
European Communication mailed Jan. 27, 2012 in co-pending European Patent Application No. 07831039.8.
International Search Report dated Jan. 29, 2008 in co-pending international patent application No. PCT/JP2007/071305.
International Search Report dated Dec. 9, 2008 in co-pending international patent application No. PCT/JP2008/067413.
Chinese Communication, with English translation, dated Oct. 10, 2011 in co-pending Chinese Patent Application No. 200880109404.7.
Japanese Communication, with partial English translation, mailed May 14, 2013 in co-pending Japanese patent application No. JP 2009-534401.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
European Communication mailed May 24, 2013 in co-pending European patent application No. 09722008.1.
International Search Report, dated Jul. 21, 2009 in co-pending PCT application No. PCT/JP2009/058325.
International Search Report dated Aug. 10, 2010 in co-pending PCT application No. PCT/JP2010/058034.
Chinese Communication, with English translation, mailed Feb. 22, 2013 in co-pending Chinese Patent Application No. 201080021960.6.
International Search Report and Written Opinion mailed Jan. 24, 2012 in corresponding PCT application No. PCT/JP2011/076373.
Office Action dated Jan. 21, 2009 in co-pending U.S. Appl. No. 10/548,988.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Final Rejection mailed Apr. 7, 2014 in co-pending U.S. Appl. No. 12/922,747.
Chinese communication, with English translation, mailed Jun. 17, 2014 in co-pending Chinese patent application No. 200980110087.5.
Office Action mailed Aug. 25, 2014 in co-pending U.S. Appl. No. 11/662,834.
Notice of Allowance mailed Sep. 11, 2014 in co-pending U.S. Appl. No. 12/226,962.
Examiner's Answer to Appeal Brief mailed Jul. 29, 2014 in co-pending U.S. Appl. No. 12/311,086.
Final Rejection mailed Jan. 10, 2014 in co-pending U.S. Appl. No. 13/319,175.
Notice of Allowance mailed Jan. 16, 2014 in co-pending U.S. Appl. No. 12/678,620.
Notice of Allowance mailed May 15, 2014 in co-pending U.S. Appl. No. 13/319,175.
Japanese communication, with English translation, mailed Jul. 8, 2014 in co-pending Japanese patent application No. 2010-503871.
Office Action mailed Oct. 1, 2014 in co-pending U.S. Appl. No. 14/241,924.
Notice of Allowance mailed Oct. 8, 2014 in co-pending U.S. Appl. No. 12/922,747.
European communication dated Oct. 29, 2014 in co-pending European patent application No. 09742696.9.
Office Action mailed Nov. 24, 2014 in co-pending U.S. Appl. No. 14/497,703.
Japanese communication, with English translation, mailed Sep. 24, 2013 in co-pending Japanese patent application No. JP 2010-503871.
Office Action mailed Oct. 7, 2013 in co-pending U.S. Appl. No. 10/548,998.

(56) References Cited

OTHER PUBLICATIONS

Canadian Communication issued Jun. 26, 2013 in co-pending Canadian patent application No. CA 2,664,852.
International Preliminary Report on Patentability, with English translation, issued Apr. 7, 2009 and Apr. 22, 2009 in co-pending PCT application No. PCT/JP2007/068841.
Final Rejection mailed Aug. 28, 2013 in co-pending U.S. Appl. No. 12/311,086.
Office Action mailed Sep. 6, 2013 in co-pending U.S. Appl. No. 12/922,747.
The Merck Index, Fourteenth Edition, 2006, p. 1-16, O'Neil, et al.
English translation of JP 6-206815 (Jul. 26, 1994), "Pharmaceutical Preparation Based on Block Copolymer-Anticancer Drug Complex", by Masayuki Yokoyama, et al., 24 pages, US Patent and Trademark Office, Aug. 2007, Translated by: FLS, Inc.
Office Action mailed Dec. 31, 2014 in co-pending U.S. Appl. No. 13/971,036.
Final Rejection mailed Mar. 4, 2015 in co-pending U.S. Appl. No. 11/662,834.

* cited by examiner

POLYMER DERIVATIVE OF CYTIDINE METABOLIC ANTAGONIST

TECHNICAL FIELD

The present invention relates to a novel polymer derivative of a cytidine metabolic antagonist, particularly a polymer derivative of a cytidine metabolic antagonist in which an amino group at the position 4 of the cytidine metabolic antagonist is bonded via a certain linker to a side-chain carboxy group of a block copolymer of a polyethylene-glycol structural moiety and a polymer having 10 or more carboxy groups, and use thereof.

BACKGROUND ART

For the purpose of treating a malignant tumor or viral disease, various cytidine metabolic antagonists have been developed, and cytarabine, gemcitabine and the like are clinically used as an anticancer agent, and zalcitabine, lamivudine and the like are clinically used as an anti-virus agent.

However, these cytidine metabolic antagonists are vulnerable to metabolism or excretion in vivo although they have strong activity in vitro, which often leads to no sufficient manifestation of the medicinal effects, or the necessity of higher dose. For example, gemcitabine has in vitro cytostatic activity comparable to a medicament such as paclitaxel and doxorubicin, which is an anticancer agent as well, but is clinically needed in a dose of 1000 mg/m$^2$ per body surface area each time. It is contemplated that this is because the amino group of the cytosine base at the position 4 is subject to metabolism by a cytidine deamination enzyme, which is a metabolic enzyme of 2'-deoxycytidine, which leads to decrease of in vivo availability as gemcitabine (see Non-Patent Document 1).

Non-Patent Document 2 describes a polymer derivative in which polyglutamic acids having about 30,000 of the average molecular weight is bonded to cytarabine. However, as the case may be, the polymer derivative of a medicament may cause hyper-reactive reaction by the immune reaction, and in such a case, may not be administered repeatedly as a medicament.

Patent Document 1 discloses a polymer derivative in which a cytidine-based derivative is bonded to polyethylene glycols, and Non-Patent Document 3 discloses a polymer derivative in which both ends of polyethylene glycols are substituted with aspartic acid in a branched shape, and cytarabine is bonded thereto. However, with these polymer derivatives, only 1 to 8 molecules or so of the medicament may be bonded to per one molecule of the polyethylene glycols, and thus the total amount of the polymer becomes large in order to administer the effective amount. Furthermore, the release of the medicament from these polymer derivatives is dependent in a portion on the hydrolysis reaction by an enzyme in vivo, and the clinically therapeutic effects are likely to be greatly influenced by individual difference of patients.

Patent Document 2 describes that a molecule, in which a medicament is bonded to a block copolymer from condensation of polyethylene glycols and polyaspartic acid, forms a micelle to become a medicine. In addition, Patent Document 3 describes a polymer carrier, which is a polymer vehicle in which a hydrophobic substance is bonded to the side-chain carboxy group of a block copolymer of polyethylene glycols and polyacidic amino acid. Furthermore, Patent Document 4 describes a polymer derivative in which an anticancer agent is bonded to the side-chain carboxy group of glutamic acid of a block copolymer from condensation of polyethylene glycols and polyglutamic acid. However, the Patent Publications 2 to 4 do not describe a cytidine metabolic antagonist as a medicament to be bonded.

Patent Document 5 describes a polymer derivative in which the side-chain carboxy group of a block copolymer of polyethylene glycols and polyglutamic acid is amide-bonded to an amino group of a cytidine metabolic antagonist. In addition, Patent Document 6 describes a polymer derivative in which the side-chain carboxy group of a block copolymer of polyethylene glycols and polyglutamic acid is ester-bonded to the hydroxy group of a nucleoside derivative that is a nucleic acid-based metabolic antagonist. However, in these documents, the cytidine metabolic antagonist is directly bonded to the carboxy group of the copolymer of the polyethylene glycol and polycarboxylic acid, but the cytidine metabolic antagonist is not bonded via any linker.

Patent Document 7 describes a polymer derivative in which a nucleoside derivative that is a nucleic acid-based metabolic antagonist is bonded via a linker having high hydrophobicity to the side-chain carboxy group of a block copolymer of polyethylene glycols and polyglutamic acid. However, this linker is not a structural moiety of succinic acid monoamide, and the polymer derivative is not a system to release the medicament along with formation of an imide.

PRIOR ART DOCUMENTS

Patent Documents

Patent Document 1: JP 2003-524028 A
Patent Document 2: JP 2694923 B
Patent Document 3: JP 3268913 B
Patent Document 4: JP 5-955 A
Patent Document 5: WO 2006/120914 A
Patent Document 6: WO 2008/056596 A
Patent Document 7: WO 2008/056654 A

Non-Patent Documents

Non-Patent Document 1: Cancer Science, published by The Japanese Cancer Association, 2004, Vol. 95, pp. 105-111
Non-Patent Document 2: Cancer Research (USA), published by US Cancer Association, 1984, Vol. 44, pp. 25-30
Non-Patent Document 3: Journal of Controlled Release (UK), published by Elsevier, 2002, Vol. 79, pp. 55-70

SUMMARY OF INVENTION

Problem to be solved by the invention

The purpose of the present invention is to provide a novel anticancer agent or anti-virus agent having higher medicinal effects than conventional ones by means of polymer derivatization of a cytidine metabolic antagonist.

Means for Solving the Problem

The present inventors have conducted extensive researches to solve the problems described above, and as results, found a polymer derivative of a cytidine metabolic antagonist in which an amino group at the position 4 of a cytidine metabolic antagonist, is bonded via a certain linker having the structure of succinic acid monoamide to the side-chain carboxy group of a block copolymer of a polyethylene-glycol structural moiety and a polymer having 10 or more carboxy groups, particularly, a block copolymer of polyethylene glycol-polyglutamic acid. The polymer derivative of the present invention has properties in that by suitably selecting an amine component that is an element of the linker, it is possible to freely regulate the release rate of the cytidine metabolic antagonist to be bonded, and render the polymer derivative of the present invention to have high medicinal effects.

Specifically, the present invention relates to (1) to (10) described below.

(1) A polymer derivative of a cytidine metabolic antagonist in which a substituent represented by the general formula (I) or the general formula (II)

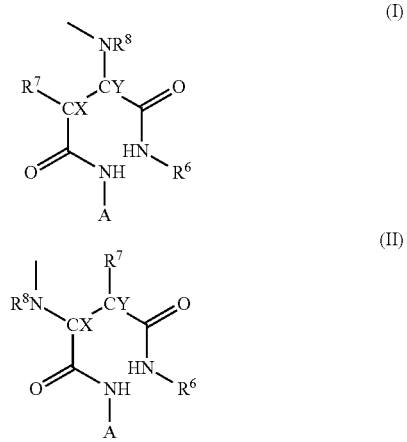

[wherein, $R^7$ and $R^8$ each independently represent a hydrogen atom or a (C1-C6)alkyl group, $R^6$ represents a hydrogen atom, an optionally substituted (C1-C40)alkyl group, an optionally substituted (C1-C40)aralkyl group, an optionally substituted aromatic group, an amino acid residue in which the carboxy group is protected, or an optionally substituted sugar residue, CX—CY represents CH—CH or C=C (double bond), and A represents the residue of the cytidine metabolic antagonist except the amino group at the position 4] is bonded to the side-chain carboxy group of a block copolymer of a polyethylene-glycol structural moiety and a polymer having 10 or more carboxy groups.

(2) The polymer derivative of a cytidine metabolic antagonist as described in the (1), in which the polymer having 10 or more carboxy groups is polyamino acid or a derivative thereof.

(3) The polymer derivative of a cytidine metabolic antagonist as described in the (2), in which the polyamino acid is polyglutamic acid.

(4) The polymer derivative of a cytidine metabolic antagonist as described in any one of the (1) to (3), in which the polymer derivative of a cytidine metabolic antagonist is a compound represented by the general formula (III)

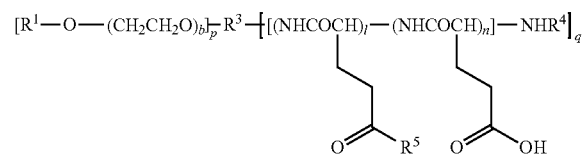

[wherein, $R^1$ represents a hydrogen atom or a (C1-C6)alkyl group, $R^3$ represents a linking group, $R^4$ represents a hydrogen atom or a (C1-C6)acyl group, $R^5$ represents a substituent represented by the general formula (I) or the general formula (II)

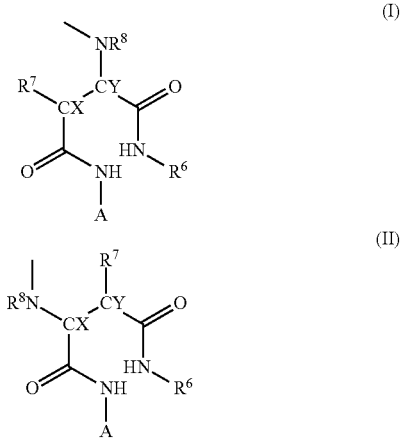

[wherein, $R^6$, $R^7$ and $R^8$, CX—CY and A are as described above], b represents an integer of 5 to 11,500, p and q each independently represent an integer of 1 to 3, i represents an integer of 5 to 200, n represents an integer of 0 to 200, and i+n represents an integer of 10 to 300].

(5) The polymer derivative of a cytidine metabolic antagonist as described in the (4), in which $R^1$ is a (C1-C3)alkyl group, $R^3$ is a linking group represented by the formula (IV), (V) or (VI)

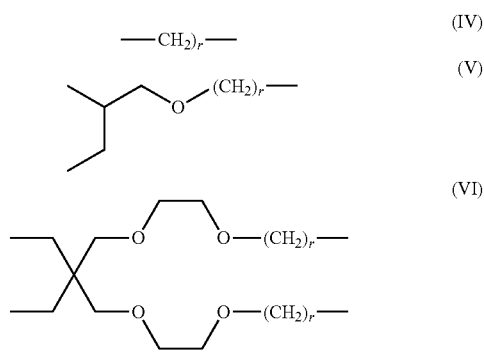

[wherein, r represents an integer of 1 to 6], $R^4$ is a (C1-C3) acyl group, b is an integer of 100 to 300, p and q is each 1 or 2 depending on $R^3$, i is an integer of 5 to 90, n is an integer of 0 to 90, and i+n is an integer of 10 to 100.

(6) The polymer derivative of a cytidine metabolic antagonist as described in the (5), in which $R^1$ is a methyl group, $R^3$ is a trimethylene group, $R^4$ is an acetyl group, both of $R^7$ and $R^8$ in $R^5$ are a hydrogen atom, and CX—CY is CH—CH.

(7) The polymer derivative of a cytidine metabolic antagonist as described in any one of the (1) to (6), in which the cytidine metabolic antagonist is gemcitabine, 5'-deoxy-5-fluorocytidine, cytarabine or 3'-ethynylcytidine.

(8) An anticancer agent containing the polymer derivative of a cytidine metabolic antagonist as described in any one of the (1) to (7) as an active ingredient.

(9) An anti-virus agent containing the polymer derivative of a cytidine metabolic antagonist as described in any one of the (1) to (7) as an active ingredient.

(10) The polymer derivative of a cytidine metabolic antagonist as described in any one of the (1) to (9), the polymer derivative forming a micelle in water.

Effects of the Invention

The polymer derivative of the cytidine metabolic antagonist of the present invention, particularly, the polymer derivative in which the amino group at the position 4 of the cytidine metabolic antagonist is bonded via a certain linker to the side-chain carboxy group of a block copolymer of polyethylene glycol and polyglutamic acid, is a polymer compound allowing uniform and easy manufactural control due to one kind of the bonding mode of the cytidine metabolic antagonist, and is expected to exert high medicinal effects. In addition, the polymer derivative of the present invention allows the release of the cytidine metabolic antagonist, independently of a hydrolysis enzyme of a living body under physiological conditions, and thus exhibits effective medicinal effects without being influenced by the individual difference. Furthermore, by suitably selecting the amine component, which is an element of the linker, it is possible to regulate the release rate of the cytidine metabolic antagonist to be bonded in accord with the purpose of the medicament to be used.

MODE FOR CARRYING OUT THE INVENTION

Figure 1:
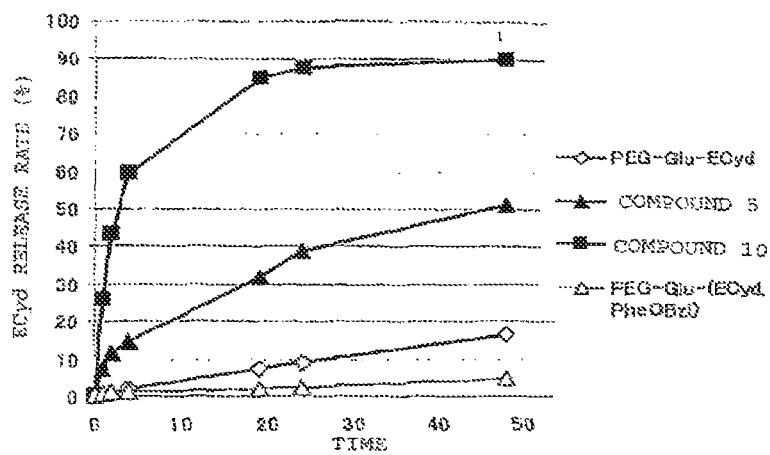
FIG. 1 represents the ratio of the release amount of 3'-ethynylcytidine (ECyd) for Compound 5 and Compound 10 of Examples, and the comparative compounds (PEG-Glu-ECyd, PEG-Glu-(ECyd, PheOBzl)) at 37° C. in a PBS solution (phosphate buffered saline, pH 7.4) with respect to the total bonding amount.

The polymer derivative of the cytidine metabolic antagonist of the present invention is such that a substituent represented by the general formula (I) or the general formula (II) [wherein, $R^7$ and $R^8$ each independently represent a hydrogen atom or a (C1-C6)alkyl group, $R^6$ represents a hydrogen atom, an optionally substituted (C1-C40)alkyl group, an optionally substituted (C1-C40)aralkyl group, an optionally substituted aromatic group, an amino acid residue in which the carboxy group is protected, or an optionally substituted sugar residue, CX—CY represents CH—CH or C=C (double bond), and A represents the residue of the cytidine metabolic antagonist except the amino group at the position 4] is bonded to the side-chain carboxy group of a block copolymer of the polyethylene-glycol structural moiety and the polymer having 10 or more carboxy groups.

Examples of the polymer having 10 or more carboxy groups in the block copolymer of the polyethylene-glycol structural moiety and the polymer having 10 or more carboxy groups in the polymer derivative of a cytidine metabolic antagonist of the present invention may include, but not limited to, polymers constituted by polymerization of a low-molecular monomer having a carboxy group in the side-chain; or polymers obtained by introducing a carboxy group using, for example, halogenoacetic acid and the like to a polymer of low-molecular monomers having functional groups such as a hydroxy group besides a carboxy group.

Examples of the polymer having a carboxy group, or the polymer that may be used in manufacture of the polymer having a carboxy group may include, but not limited to, polyglutamic acid, polyaspartic acid, polyserine, polycysteine, polytyrosine, polylysine, polymalic acid, dextran or a partial oxidant thereof, and polyuronic acid.

Examples of the polymer having a carboxy group may preferably include, but not limited to, polyamino acids or a derivative thereof, and particularly the polymer having a carboxy group is preferably polyglutamic acid, which is a polyacidic amino acid.

The polyethylene-glycol structural moiety in the block copolymer of the polyethylene-glycol structural moiety and the polymer having 10 or more carboxy groups in the polymer derivative of a cytidine metabolic antagonist of the present invention is not particularly limited as long as the polymer derivative has 1 to 15,000 or so of the structural moiety of ethylene glycol. The polyethylene-glycol structural moiety is preferably a structural moiety containing linear polyethylene glycol and a linking group to the polymer having 10 or more carboxy groups.

The block copolymer of the polyethylene-glycol structural moiety and the polymer having 10 or more carboxy groups in the polymer derivative of a cytidine metabolic antagonist of the present invention is preferably a block copolymer of the polyethylene-glycol structural moiety and polyglutamic acid.

$R^7$ and $R^8$ in the substituent of the general formula (I) or the general formula (II) that are bonded to the polymer having 10 or more carboxy groups of the polymer derivative of a cytidine metabolic antagonist of the present invention, are each independently a hydrogen atom or a (C1-C6)alkyl group. Examples of the (C1-C6)alkyl group may include, but not limited to, a methyl group, an ethyl group, an n-propyl group, an isopropyl group, an n-butyl group, an s-butyl group, a t-butyl group, an n-pentyl group, an n-hexyl group, a cyclopropyl group, a cyclopentyl group, and a cyclohexyl group.

$R^7$ and $R^8$ in the substituent is particularly preferably a hydrogen atom for both of them.

$R^6$ in the substituent is a hydrogen atom, an optionally substituted (C1-C40)alkyl group, an optionally substituted (C1-C40)aralkyl group, an optionally substituted aromatic group, an amino acid residue in which the carboxy group is protected, or an optionally substituted sugar residue.

The (C1-C40)alkyl group in the optionally substituted (C1-C40)alkyl group may be linear or branched, and examples thereof include, for example, a methyl group, an ethyl group, an n-propyl group, an isopropyl group, an n-butyl group, an s-butyl group, an isobutyl group, an n-pentyl group, an n-hexyl group, an n-stearyl group and the like. Examples of the substituent may include, but not limited to, a phenyl group, a naphthyl group, a methoxy group, an ethoxy group, a dimethylamino group, and an adamantyl group. The substitution position is not particularly limited as long as it allows the substitution.

The (C1-C40)aralkyl group in the optionally substituted (C1-C40)aralkyl group is not particularly limited as long as it is an alkyl group bonded to an aromatic hydrocarbon group, and examples of thereof include, for example, a benzyl group, a naphthylmethyl group, a phenethyl group, a 4-phenylbutyl group and the like. Examples of the substituent of the moiety of the aromatic hydrocarbon group may include, but not limited to, a methyl group, an ethyl group, a nitro group, a chlorine atom, a bromine atom, and a dimethylamino group. The substitution position and the substituent number are not particularly limited as long as they allow the substitution.

Examples of the optionally substituted aromatic group may include, but not limited to, substituents derived from benzene, naphthalene, florene, aniline, nitroaniline, chloroaniline, aminofluorobenzonitrile, aminonaphthalene, aminoflavone, and aminoflorene. The bonding position of the substituent derived from the aromatic compound to the substituent of the general formula (I) or the general formula (II) is not particularly limited as long as it allows the substitution.

Examples of the amino acid of the amino acid residue in which the carboxy group is protected may include, but not limited to, amino acids that are used in normal peptide synthesis in which the carboxy group is protected. The amino acid of the amino acid residue is preferably a compound in which the carboxy group of the amino acid is protected with ester or amide, for example, (C1-C12)alkyl ester of alanine, α- or β-(C1-C12)alkyl ester of aspartic acid, α- or γ-(C1-C12) alkyl ester of glutamic acid, (C1-C12)alkyl ester of phenylalanine, (C1-C12)alkyl ester of cysteine, (C1-C12)alkyl ester of glycine, (C1-C12)alkyl ester of leucine, (C1-C12)alkyl ester of isoleucine, (C1-C12)alkyl ester of histidine, (C1-C12)alkyl ester of proline, (C1-C12)alkyl ester of serine, (C1-C12)alkyl ester of threonine, (C1-C12)alkyl ester of valine, (C1-C12)alkyl ester of triptophan, (C1-C12)alkyl ester of tyrosine and the like, or substitution products thereof by a phenyl group and the like, and particularly preferably, phenylalanine methyl ester, glycine methyl ester, glycine (4-phenyl-1-butanol)ester, leucine methyl ester, phenylalanine benzyl ester, phenylalanine (4-phenyl-1-butanol)ester and the like. The amino acid may be the D form or the L form, or a mixture thereof.

The sugar of the optionally substituted sugar residue is not particularly limited as long as it is an amino sugar, and examples thereof include, for example, glucosamine, galactosamine, mannosamine and the like. Examples of the substituent may include, but not limited to, an acetyl group, a pivaloyl group, a benzyl group, and a methyl group. The sugar may be the D form or the L form, or a mixture thereof. In addition, the substitution position and the substituent number of the substituent are not limited as long as they allow the substitution.

The CX—CY in the substituent of the general formula (I) or the general formula (II) that acts as a linker in the polymer derivative of a cytidine metabolic antagonist of the present invention may be good as long as the linker moiety may form a circular imide intermediate, and is CH—CH or C=C (double bond). Examples thereof include, for example, succinic acid monoamide derivative, maleic acid monoamide derivative and the like. Particularly, the CX—CY is preferably CH—CH.

Examples of the cytidine metabolic antagonist (A-NH$_2$) that is amide-bonded to the linker at the position 4 of the amino group of the cytosine base in the polymer derivative of a cytidine metabolic antagonist of the present invention may include, but not limited to, gemcitabine, 5'-deoxy-5-fluorocytidine, cytarabine and 3'-ethynylcytidine.

The structural formulae of gemcitabine, 5'-deoxy-5-fluorocytidine, cytarabine and 3'-ethynylcytidine are described below.

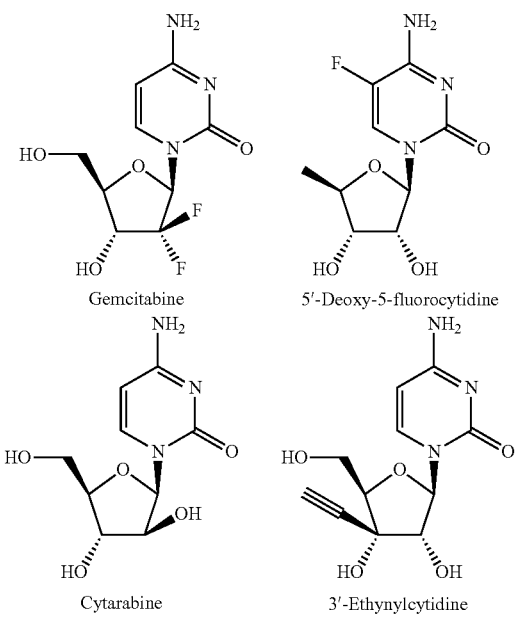

Gemcitabine 5'-Deoxy-5-fluorocytidine
Cytarabine 3'-Ethynylcytidine

The polymer derivative of a cytidine metabolic antagonist of the present invention is preferably a compound represented by the general formula (III) described above [wherein, $R^1$ represents a hydrogen atom or a (C1-C6)alkyl group, $R^3$ represents a linking group, $R^4$ represents a hydrogen atom or a (C1-C6)acyl group, $R^5$ represents a substituent represented by the general formula (I) or the general formula (II) [wherein, $R^6$, $R^7$ and $R^8$, CX—CY and A are as described above], b represents an integer of 5 to 11,500, p and q each independently represent an integer of 1 to 3, i represents an integer of 5 to 200, n represents an integer of 0 to 200, and i+n represents an integer of 10 to 300].

Examples of the (C1-C6)alkyl group in $R^1$ may include, but not limited to, linear or branched (C1-C6)alkyl groups, and preferably (C1-C4)alkyl groups, for example, a methyl group, an ethyl group, an n-propyl group, and an n-butyl group.

Particularly, $R^1$ in the formula (III) is preferably a methyl group.

The (C1-C6)acyl group in $R^4$ is not particularly limited, but preferably is a (C1-C3)acyl group, for example, a formyl group, an acetyl group, a propionyl group and the like.

Particularly, $R^4$ in the formula (III) is preferably an acetyl group.

$R^5$ is a substituent represented by the general formula (I) or the general formula (II), and the substituent is as described above, and the preferable group is also as described above.

The linking group of $R^3$ is a structural moiety that constitutes the end portion of the bonding side of the polyethyleneglycol structural moiety to the polymer having 10 or more carboxy groups in the block copolymer of the polyethyleneglycol structural moiety and the polymer having 10 or more carboxy groups, and is a linear or branched (C1-C20)alkylene group that may be through a heteroatom. Examples of the heteroatom may include, but not limited to, an oxygen atom, a nitrogen atom, and a sulfur atom.

Examples of the linking group may include, but not limited to, groups represented by the formula (IV), the formula (V) and the formula (VI) described above. Herein, r, the methylene number, is an integer of 1 to 6, preferably 2 to 4, and most preferably 3.

Particularly, the linking group of $R^3$ is preferably a trimethylene group represented by the formula (IV) [r=3].

p and q in the general formula (III) are each independently an integer of 1 to 3, and prescribed by the linking group of $R^3$. For example, when the linking group is a group represented by the formula (IV), p=q=1; when the linking group a group represented by the formula (V), p=2 and q=1; and when the linking group is a group represented by the formula (VI), p=2 and q=2.

b in the general formula (III) is an integer of 5 to 11,500 or so, preferably an integer of 8 to 2,300 or so, and further preferably an integer of 100 to 300 or so. The molecular weight of the polyethylene-glycol structural moiety is 300 to 500,000 or so, preferably 500 to 100,000 or so, and further preferably 1,000 to 50,000 or so. Meanwhile, the molecular weight in the present invention is a weight-average molecular weight measured with GPC method.

i in the general formula (III) is an integer of 5 to 200 and preferably 5 to 90, n is an integer of 0 to 200 and preferably 0 to 90, and the total glutamic acid number (i+n) is an integer of 10 to 300, preferably 10 to 100 or so, and most preferably 10 to 60 or so. The ratio of the bonded glutamic acid number (i) of the cytidine metabolic antagonist with respect to the total glutamic acid number (i+n) is 10 to 100%, preferably 20 to 100%, and further preferably 40 to 100%.

Each component of the polyglutamic acid in the general formula (III) is not limited by the bonding order thereof, and may be of a block type or random type.

The molecular weight of the polymer derivative of a cytidine metabolic antagonist of the present invention is 1,000 to 600,000 or so, preferably 1,100 to 110,000 or so, and further preferably 1,500 to 80,000 or so.

The substituent of the general formula (I) or the general formula (II) in the polymer derivative of a cytidine metabolic antagonist of the present invention may be present as mixed or alone, respectively in one molecule, and the groups of $R^6$, $R^7$ and $R^8$ may be the same or different in one molecule.

The polymer derivative of a cytidine metabolic antagonist of the present invention may form a micelle in which the polyethylene-glycol structural moiety forms the outer shell in water, and the hydrophobic polymer to which the cytidine metabolic antagonist is bonded via the linker, may form the inner shell.

The manufacture of the polymer derivative of a cytidine metabolic antagonist of the present invention will be illustrated below. However, the manufacture method is not limited thereto.

First, the cytidine metabolic antagonist derivative is manufactured, which is attached to the linker moiety represented by the general formula (I) or the general formula (II) described above. Specifically, a succinic acid monoamide derivative having a protected amino group and a carboxy group, or a maleic acid monoamide derivative having a protected amino group and a carboxy group, and a cytidine metabolic antagonist are rendered to form an amide bond to the amino group at the position 4 of the cytidine metabolic antagonist using a dehydration condensation agent in an organic solvent, and the protecting group is deprotected, whereby to obtain a succinic acid monoamide derivative having an amino group to which the cytidine metabolic antagonist is bonded, or a maleic acid monoamide derivative having an amino group to which the cytidine metabolic antagonist is bonded.

Next, the derivative is rendered to form an amide bond to the side-chain carboxy group of a block copolymer of the polyethylene-glycol structural moiety and polyglutamic acid, which is described in a document or obtained by applying the method, using a dehydration condensation agent in an organic solvent.

The manufacture of the polymer derivative of a cytidine metabolic antagonist of the present invention will be explained further specifically. For example, a succinic acid monoamide derivative in which the amino group is protected with tert-butoxycarbonyl group (Boc), and 3'-ethynylcytidine are dissolved in an organic solvent in which both of them are dissolved, preferably a non-protonic polar solvent such as N,N-dimethylformamide (DMF), 1,3-dimethyl-2-imidazolidinone (DMI) and N-methylpyrolidone (NMP), and subjected to a reaction at 0 to 180° C. preferably 5 to 50° C. using a dehydration condensation agent such as dicyclohexylcarbodiimide (DCC), diisopropylcarbodiimide (DIPCI), 1-ethyl-3-(3-dimethylaminopropyl)carbodiimide (WSC) hydrochloride, 1-ethoxycarbonyl-2-ethoxy-1,2-dihydroxyquinolinone (EEDQ), 4-(4,6-dimethoxy-1,3,5-triazin-2-yl)-4-methylmorpholinium chloride (DMT-MM), O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), (1-cyano-2-ethoxy-2-oxoethylidene aminooxy) dimethylamino-2-morpholino-carbenium hexafluorophosphate (COMU), whereby to obtain a condensate. An isolation purification process may be performed if necessary depending on the reactants to obtain an amide-bonded body with the amino group at the position 4 of the cytosine base. In addition, a manufacture method using diisopropylcarbodiimide (DIPCI) or 1-ethyl-3-(3-dimethylaminopropyl)carbodiimide (WSC) hydrochloride as a dehydration condensation agent, and 1-hydroxy-1H-benzotriazol(HOBt) or 1-hydroxy-7-azabenzotriazol(HOAt) as a reaction aid, or using only 1-ethoxycarbonyl-2-ethoxy-1,2-dihydroxyquinolinone (EEDQ), 4-(4, 6-dimethoxy-1,3,5-triazin-2-yl)-4-methylmorpholinium chloride (DMT-MM), (1-cyano-2-ethoxy-2-oxoethylidene aminooxy)dimethylamino-2-morpholinocarbenium hexafluorophosphate (COMU) as a dehydration condensation agent is practically preferable since it allows to preferentially manufacture intended amide-bonded body with the amino group at the position 4 of the cytosine base. Furthermore, other functional groups than the carboxy group reacting with the cytidine metabolic antagonist may be protected before being subjected to the condensation reaction, and deprotected at an appropriate stage after the reaction.

Next, the Boc is deprotected, and the condensate is amide-bonded with a block copolymer of methoxy polyethylene glycol-polyglutamic acid, which is prepared by the method described in the pamphlet of WO 2006/120914 A, in the similar solvent as described above, using the similar dehydration condensation agent as described above, and using the reaction aid as necessary, whereby to obtain the polymer derivative of a cytidine metabolic antagonist of the present invention.

The polymer derivative of a cytidine metabolic antagonist of the present invention may be used as a medicine for the indications of diseases corresponding to the medicinal effects of the cytidine metabolic antagonist to be bonded, for example, as an anticancer agent, anti-virus agent or the like. Such use is also encompassed in the present invention. The polymer derivative may be used as a dosage form ordinarily used, such as an injection, a tablet and powders. Pharmaceutically acceptable, ordinarily used carriers, for example, a binder, a lubricant, a disintegrant, a solvent, an excipient, a solubilizer, a dispersing agent, a stabilizer, a suspending agent, a preservative, a soothing agent, a pigment, a flavoring agent and the like may be used in the formulation.

The polymer derivative of a cytidine metabolic antagonist of the present invention is preferably used as an injection, and is ordinarily used as dissolved in, for example, water, physiological saline, 5% glucose or mannitol solution, an aqueous organic solvent (for example, glycerol, ethanol, dimethylsulfoxide, N-methylpyrolidone, polyethylene glycol, Cremophor and the like and a mixed solution thereof) and a mixed solution of water and the aqueous organic solvent, and the like.

The dose of the polymer derivative of a cytidine metabolic antagonist of the present invention may vary naturally depending on the properties of the cytidine metabolic antagonist, the sex, the age, the physiological state, the indication or the clinical conditions of a patient, but parentally administered, ordinarily in 0.01 to 500 mg/m$^2$, preferably 0.1 to 250 mg/m$^2$ as an active ingredient per one day for an adult. The administration by injection is performed intravenously, arterially, or to the affected area (tumor area) and the like.

In use of the polymer derivative of a cytidine metabolic antagonist of the present invention, 2 or more compounds that is incorporated into the polymer derivative of a cytidine metabolic antagonist of the present invention may be used in a mixture.

EXAMPLES

Hereinafter, the present invention will be further explained with Examples. However, the present invention is not limited to these Examples. Meanwhile, when the compound of the present invention forms particles such as a micelle in an aqueous solution in Examples, the size of the particles (particle size) is indicated with Gaussian distribution analysis by dynamic light scattering method or by static light scattering method as RMS radius. The former was measured with Zeta Potential/Particle sizer NICOMP™ 380ZLS (manufactured by Particle Sizing Systems), and the latter was measured with DAWN EOS™ (manufactured by Wyatt Technology), and calculated.

Synthesis Example 1

Synthesis of N-(tert-butoxycarbonyl)aspartic acid-1-phenylbutyl amide-4-benzyl ester (Compound 1)

4.27 g of N-(tert-butoxycarbonyl)aspartic acid-4-benzyl ester (manufactured by PEPTIDE INSTITUTE, INC.) and 2.1 mL of 1-phenylbutyl amine were dissolved in 40 mL of DMF, and then 2.70 g of WSC hydrochloride and 1.93 g of HOBt were added thereto, and the reaction solution was stirred at room temperature for 6 hours. The reaction solution was added with water, and extracted with ethyl acetate. The organic layer was washed with a saturated aqueous solution of sodium hydrogen carbonate, dried with magnesium sulfate, and then distilled under reduced pressure to remove ethyl acetate, and then dried under vacuum, thereby to give 3.94 g of Compound 1.

MS: m/z 477 (M+Na)$^+$: 477 of calculated value as $C_{26}H_{34}N_2O_5$ (M+Na)$^+$

Synthesis Example 2

Synthesis of N-(tert-butoxycarbonyl)aspartic acid-1-phenylbutyl amide (Compound 2)

3.50 g of Compound 1 obtained in Synthesis Example 1 was dissolved in 15 mL of ethyl acetate, and 0.656 g of 5% palladium carbon (50% moisture content) was added thereto. Then, the inside of the reaction system was substituted with hydrogen, and the reaction system was stirred at room temperature overnight and subjected to hydrogenolysis. The 5% palladium carbon was filtered off, and washed with 80 mL of ethyl acetate. Then, the organic layers were combined, distilled under reduced pressure to remove ethyl acetate, and then dried under vacuum, thereby to give 2.58 g of Compound 2.

MS: m/z 387 (M+Na)$^+$: 387 of calculated value as $C_{19}H_{28}N_2O_5$ (M+Na)$^+$

Synthesis Example 3

Synthesis of N-(tert-butoxycarbonyl)aspartic acid-1-phenylbutyl amide-4-(3'-ethynylcytidine) amide (Compound 3)

754 mg of Compound 2 obtained in Synthesis Example 2, 500 mg of 3'-ethynylcytidine and 275 mg of HOBt were dissolved in 4 mL of DMF, and then the inside of the reaction system was substituted with argon, 353 mg of WSC hydrochloride was added thereto, and the reaction solution was stirred at 20° C. for 10 hours. Then, 377 mg of Compound 2 and 177 mg of WSC hydrochloride were added thereto, and the reaction solution was stirred at 20° C. for 3 hours, and subsequently 177 mg of WSC hydrochloride was added thereto, and the reaction solution was stirred at 20° C. for 2 hours, and further, 189 mg of Compound 2 and 177 mg of WSC hydrochloride were added thereto, and the reaction solution was stirred at 20° C. for 2 hours. The reaction solution was added with water and extracted with ethyl acetate. The organic layer was washed with a saturated aqueous solution of ammonium chloride, a saturated aqueous solution of sodium hydrogen carbonate and a saturated aqueous solution of sodium chloride in this order. The resultant was dried with magnesium sulfate, and then distilled under reduced pressure to remove ethyl acetate, and the obtained oily substance was purified with silica gel column chromatography (CHCl$_3$/MeOH), to give 716 mg of Compound 3.

$^1$H-NMR (400 MHz, DMSO-d$_6$, ppm): 1.35 (s, 9H), 1.3-1.6 (m, 4H), 2.55 (m, 2H), 2.6-2.7 (m, 2H), 3.06 (m, 2H), 3.16 (s, 1H), 3.54 (s, 1H), 3.6-3.7 (m, 2H), 3.96 (m, 1H), 4.14 (d, 1H), 4.3 (br, 1H), 5.0 (br, 1H), 5.87 (d, 1H), 5.93 (br, 1H), 7.01 (d, 1H), 7.1-7.2 (m, 5H), 7.80 (br, 1H), 8.31 (d, 1H), 10.87 (s, 1H)

MS: m/z 614 (M+H)$^+$: 614 of calculated value as $C_{29}H_{37}N_5O_9$ (M+H)$^+$

Synthesis Example 4

Synthesis of aspartic acid-1-phenylbutyl amide-4-(3'-ethynylcytidine)amide (Compound 4)

860 mg of Compound 3 obtained in Synthesis Example 3 was dissolved in 3.5 mL of ethyl acetate, and then 3.5 mL of 4N—HCl/AcOEt was added thereto, and the reaction solution was stirred at room temperature for 1 hour. After completion of the reaction, the reaction solution was distilled under reduced pressure to remove ethyl acetate, thereby to give 710 mg of Compound 4.

MS: m/z 514 (M+H)$^+$: 514 of calculated value as $C_{25}H_{31}N_5O_7$ (M+H)$^+$

Example 1

Synthesis of amide-bonded body of block copolymer including methoxy polyethylene-glycol structural moiety having 12,000 of the molecular weight and polyglutamic acid moiety having 21 of the polymerization number, to aspartic acid-1-phenylbutyl amide-4-(3'-ethynylcytidine)amide: Compound of general formula (III) wherein $R^1$=methyl group, $R^3$=trimethylene group, $R^4$=acetyl group, $R^7$ and $R^8$=hydrogen atom, $R^6$=1-phenylbutyl group, p=q=1, i+n=21 and b=273 (Compound 5)

503 mg of a block copolymer of methoxy polyethylene glycol-polyglutamic acid prepared by the method described in the pamphlet of WO 2006/120914 A was dissolved in 9 mL of DMF. 600 mg of Compound 4 obtained in Synthesis Example 4, 197 µL of triethyl amine, 227 µL of DIPCI and 96 mg of HOBt were added thereto, and the reaction solution was stirred at 20° C. for 24 hours. Furthermore, 55 µL of triethyl amine and 114 µL of DIPCI were added thereto, and the reaction solution was stirred for 3 hours, and then slowly dropped to a mixed solution of 9 mL of ethanol and 72 mL of diisopropyl ether. The reaction solution was stirred at room temperature for 1 hour, and the deposit was taken by filtration and washed with ethanol/diisopropyl ether (1/8(v/v), 20 mL). The deposit was dissolved in 12 mL of acetonitrile, slowly dropped to a mixed solution of 15 mL of ethanol and 90 mL of diisopropyl ether, and stirred at room temperature for 1 hour. The deposit was taken by filtration and washed with ethanol/diisopropyl ether (1/8(v/v), 20 mL). The deposit was dissolved in 10 mL of acetonitrile and 10 mL of water, and added with ion exchange resin (DOWEX 50($H^+$) manufactured by The Dow Chemical Company, 2 mL) and stirred, and the resin was taken by filtration and washed with acetonitrile/water (1/1(v/v), 30 mL). The obtained solution was distilled under reduced pressure to remove acetonitrile, and then freeze-dried, thereby to give 580 mg of Compound 5.

In order to find out the content of the 3'-ethynylcytidine bonded to Compound 5, an aqueous solution of 1N-sodium hydroxide was added to Compound 5, and the reaction solution was stirred at 37° C. for 1 hour, and then isolated 3'-ethynylcytidine was analyzed with HPLC (high performance liquid chromatography), and the content was calculated using the calibration curve obtained in advance from the 3'-ethynylcytidine. As the result thereof, the content of the 3'-ethynylcytidine bonded was 19.4% (w/w).

Calculation of the RMS radius was performed by Gaussian distribution analysis and static light scattering method using an aqueous solution (1 mg/mL) of Compound 5, and as results, the RMS radius was each 18 nm (volume weighting) and 11 nm. From this, it is contemplated that Compound 5 forms a micelle in water.

Synthesis Example 5

Synthesis of N-(tert-butoxycarbonyl)aspartic acid-1-butyl amide-4-benzyl ester (Compound 6)

4.27 g of N-(tert-butoxycarbonyl)aspartic acid-4-benzyl ester and 1.31 mL of n-butyl amine were dissolved in 25 mL of DMF, and then 2.93 g of WSC hydrochloride and 1.93 g of HOBt were added thereto, and the reaction solution was stirred at room temperature overnight. The reaction solution was added with water, and extracted with ethyl acetate. The organic layer was washed with a saturated aqueous solution of ammonium chloride and a saturated aqueous solution of sodium hydrogen carbonate, dried with magnesium sulfate, and then distilled under reduced pressure to remove ethyl acetate, and then dried under vacuum, thereby to give 5.12 g of Compound 6.

Synthesis Example 6

Synthesis of N-(tert-butoxycarbonyl)aspartic acid-1-butyl amide (Compound 7)

5.09 g of Compound 6 obtained in Synthesis Example 5 was dissolved in 15 mL of ethyl acetate, 0.656 g of 5% palladium carbon (50% moisture content) was added thereto, and then the inside of the reaction system was substituted with hydrogen, and the reaction system was stirred at room temperature overnight and subjected to hydrogenolysis. The 5% palladium carbon was filtered off, and washed with ethyl acetate. Then, the organic layers were combined, distilled under reduced pressure to remove ethyl acetate, and then dried under vacuum, thereby to give 4.05 g of Compound 7.

Synthesis Example 7

Synthesis of N-(tert-butoxycarbonyl)aspartic acid-1-butyl amide-4-(3'-ethynylcytidine) amide (Compound 8)

596 mg of Compound 7 obtained in Synthesis Example 6, 500 mg of 3'-ethynylcytidine and 275 mg of HOBt were dissolved in 4 mL of DMF, and then the inside of the reaction system was substituted with argon, 353 mg of WSC hydrochloride was added thereto, and the reaction solution was stirred at 20° C. for 9 hours. Then, 298 mg of Compound 7 and 177 mg of WSC hydrochloride were added thereto, and the reaction solution was stirred at 20° C. for 3 hours, and further 298 mg of Compound 7 and 177 mg of WSC hydrochloride were added thereto, and the reaction solution was stirred at 20° C. for 3 hours. The reaction solution was added with water and extracted with ethyl acetate. The organic layer was washed with a saturated aqueous solution of ammonium chloride, a saturated aqueous solution of sodium hydrogen carbonate and a saturated aqueous solution of sodium chloride in this order, dried with magnesium sulfate, and then distilled under reduced pressure to remove ethyl acetate, and the obtained oily substance was purified with silica gel column chromatography ($CHCl_3$/MeOH), thereby to give 590 mg of Compound 8.

$^1$H-NMR (400 MHz, DMSO-$d_6$, ppm): 0.85 (t, 3H), 1.2-1.3 (m, 4H), 1.36 (s, 9H), 2.5-2.7 (m, 2H), 3.03 (m, 2H), 3.53 (s, 1H), 3.6-3.7 (m, 2H), 3.96 (m, 1H), 4.14 (m, 1H), 4.28 (m, 1H), 5.08 (m, 1H), 5.87 (d, 1H), 5.92 (m, 2H), 7.00 (d, 1H), 7.20 (d, 1H), 7.75 (m, 1H), 8.32 (d, 1H), 10.86 (s, 1H)

MS: m/z 538 $(M+H)^+$: 538 of calculated value as $C23H_{33}N_5O_9 (M+H)^+$

Synthesis Example 8

Synthesis of aspartic acid-1-butyl amide-4-(3'-ethynylcytidine)amide (Compound 9)

590 mg of Compound 8 obtained in Synthesis Example 7 was dissolved in 3 mL of ethyl acetate, and then 2.7 mL of 4N—HCl/AcOEt was added thereto, and the reaction solution was stirred at room temperature for 1 hour. After completion of the reaction, the reaction solution was distilled under reduced pressure to remove ethyl acetate, thereby to give 500 mg of Compound 9.

MS: m/z 438 $(M+H)^+$: 438 of calculated value as $C19H_{27}N_5O_7 (M+H)^+$

Example 2

Synthesis of amide-bonded body of block copolymer including methoxy polyethylene-glycol structural moiety having 12,000 of the molecular weight and polyglutamic acid moiety having 21 of the polymerization number, to aspartic acid-1-butyl amide-4-(3'-ethynylcytidine)amide: Compound of general formula (III) wherein $R^1$=methyl group, $R^3$=trimethylene group, $R^4$=acetyl group, $R^7$ and $R^8$=hydrogen atom, $R^6$=1-butyl group, p=q=1, i+n=21 and b=273 (Compound 10)

438 mg of a block copolymer of methoxy polyethylene glycol-polyglutamic acid prepared by the method described in the pamphlet of WO 2006/120914 A was dissolved in 8 mL of DMF, and the reaction solution was stirred at 35° C. for 15 minutes, and then stirred at 20° C. for 1 hour. 450 mg of Compound 9 obtained in Synthesis Example 8, 172 µL of triethyl amine, 198 µL of DIPCI and 84 mg of HOBt were added thereto, and the reaction solution was stirred at 20° C. for 24 hours. Furthermore, 48 µL of triethyl amine and 99 µL of DIPCI were added thereto, and the reaction solution was stirred for 3 hours, and then slowly dropped to a mixed solution of 8 mL of ethanol and 64 mL of diisopropyl ether. The reaction solution was stirred at room temperature for 1 hour. The deposit was taken by filtration and washed with ethanol/diisopropyl ether (1/8(v/v), 18 mL). The deposit was dissolved in a mixed solvent of 1 mL of DMF and 7 mL of acetonitrile, slowly dropped to a mixed solution of 8 mL of ethanol and 64 mL of diisopropyl ether, and stirred at room temperature for 1 hour. The deposit was taken by filtration and washed with ethanol/diisopropyl ether (1/8(v/v), 18 mL). The deposit was dissolved in 13.5 mL of acetonitrile and 4.5 mL of water, and then added with ion exchange resin (DOWEX 50($H^+$) manufactured by The Dow Chemical Company, 5 mL) and stirred, and the resin was taken by filtration and washed with acetonitrile/water (1/1(v/v), 25 mL). The obtained solution was distilled under reduced pressure to remove acetonitrile, and then freeze-dried, thereby to give 560 mg of Compound 10.

The content of the 3'-ethynylcytidine bonded to Compound 10 was analyzed in a similar manner to in Example 1 using HPLC (high performance liquid chromatography) after the hydrolysis. The content of the 3'-ethynylcytidine bonded was 20.9% (w/w).

Gaussian distribution analysis was performed using an aqueous solution (1 mg/mL) of Compound 10, and as results, the scattering intensity was weak, and it was contemplated that Compound 10 did not form a micelle in water at this concentration.

Synthesis Example 9

Synthesis of N-(tert-butoxycarbonyl)aspartic acid-1-adamantane methyl amide-4-benzyl ester (Compound 11)

10.3 g of N-(tert-butoxycarbonyl)aspartic acid-4-benzyl ester and 5.17 g of 1-adamantane methyl amine were dissolved in 100 mL of DMF, and then 7.15 mg of WSC hydrochloride and 4.72 g of HOBt were added thereto, and the reaction solution was stirred at room temperature overnight. The reaction solution was added with water, and extracted with ethyl acetate. The organic layer was washed with a saturated aqueous solution of sodium hydrogen carbonate, dried with magnesium sulfate, and then distilled under reduced pressure to remove ethyl acetate, and then dried under vacuum, thereby to give 15.0 g of Compound 11.

$^1$H-NMR (400 MHz, $CDCl_3$, ppm): 1.42 (s, 6H), 1.46 (s, 9H), 1.61 (d, 3H), 1.70 (d, 3H), 1.97 (s, 3H), 2.71-2.76 (m, 1H), 2.91-2.96 (m, 2H), 3.03 (dd, 1H), 4.50 (br, 1H), 5.11 (d, 1H), 5.16 (d, 1H), 5.74 (br, 1H), 6.56 (br, 1H), 7.38-7.31 (m, 5H)

MS: m/z 493 (M+Na)$^+$: 493 of calculated value as $C27H_{38}N_2O_5$ (M+Na)$^+$

Synthesis Example 10

Synthesis of N-(tert-butoxycarbonyl)aspartic acid-1-adamantane methyl amide (Compound 12)

15.0 g of Compound 11 obtained in Synthesis Example 9 was dissolved in 75 mL of ethyl acetate, 1.5 g of 10% palladium carbon (50% moisture content) was added thereto, and then the inside of the reaction system was substituted with hydrogen, and the reaction solution was stirred at room temperature for 2 days and subjected to hydrogenolysis. The 10% palladium carbon was filtered off, and washed with 20 mL of ethyl acetate. Then, the organic layers were combined, distilled under reduced pressure to remove ethyl acetate, and then dried under vacuum, thereby to give 9.22 g of Compound 12.

$^1$H-NMR (400 MHz, $CDCl_3$, ppm): 1.46 (s, 15H), 1.61 (d, 3H), 1.70 (d, 3H), 1.96 (s, 3H), 2.71-2.77 (m, 1H), 2.89-3.06 (m, 3H), 4.49 (br, 1H), 5.76 (br, 1H), 6.77 (br, 1H)

MS: m/z 403 (M+Na)$^+$: 403 of calculated value as $C20H_{32}N_2O_5$ (M+Na)$^+$

Synthesis Example 11

Synthesis of N-(tert-butoxycarbonyl)aspartic acid-1-adamantane methyl amide-4-(3'-ethynylcytidine) amide (Compound 13)

1.88 g of Compound 12 obtained in Synthesis Example 10, 1.10 g of 3'-ethynylcytidine and 658 mg of HOBt were dissolved in 20 mL of DMF, and then the reaction solution was frozen and degassed. 914 mg of WSC hydrochloride was added thereto, and the reaction solution was stirred at 20° C. for 9 hours. Then, 313 mg of Compound 12 and 141 mg of WSC hydrochloride were added thereto, and the reaction solution was stirred at 20° C. for 2 hours. The reaction solution was added with water, and extracted with ethyl acetate. The organic layer was washed with a saturated aqueous solution of ammonium chloride and a saturated aqueous solution of sodium hydrogen carbonate, dried with magnesium sulfate, and then distilled under reduced pressure to remove ethyl acetate, and the obtained oily substance was purified with silica gel column chromatography ($CHCl_3$/n-Hexane), thereby to give 1.47 g of Compound 13.

$^1$H-NMR (400 MHz, $CDCl_3$, ppm): 1.41 (s, 9H), 1.45 (s, 6H), 1.58 (d, 3H), 1.67 (d, 3H), 1.93 (s, 3H), 2.64 (br, 2H), 2.92-3.22 (m, 5H), 4.00 (br, 1H), 4.30 (br, 1H), 4.49 (br, 1H), 4.68 (br, 1H), 5.18 (br, 1H), 5.85 (br, 1H), 5.26 (br, 1H), 7.01 (br, 1H), 7.45 (br, 1H), 7.71 (br, 1H), 8.22 (br, 1H), 10.5 (br, 1H)

MS: m/z 630 (M+H)$^+$: 630 of calculated value as $C31H_{43}N_5O_9$ (M+H)$^+$

Synthesis Example 12

Synthesis of aspartic acid-1-adamantane methyl amide-4-(3'-ethynylcytidine) amide (Compound 14)

1.47 g of Compound 13 obtained in Synthesis Example 11 was dissolved in 6 mL of ethyl acetate, and then 6 mL of 4N—HCl/AcOEt was added thereto, and the reaction solution was stirred at room temperature for 1 hour. After completion of the reaction, the reaction solution was distilled under reduced pressure to remove ethyl acetate, and then dried under vacuum, thereby to give 1.20 g of Compound 14.

$^1$H-NMR (400 MHz, CD$_3$OD, ppm): 1.57 (s, 6H), 1.70 (br, 3H), 1.79 (br, 3H), 2.00 (s, 3H), 2.82 (br, 2H), 3.15-3.20 (m, 5H), 4.05 (br, 1H), 4.22 (br, 1H), 4.36 (br, 1H), 6.04 (br, 1H), 7.37 (br, 1H), 8.60 (br, 1H)

MS: m/z 530 (M+H)$^+$: 530 of calculated value as C26H$_{35}$N$_5$O$_7$ (M+H)$^+$ Example 3

Synthesis of amide-bonded body of block copolymer including methoxy polyethylene-glycol structural moiety having 12,000 of the molecular weight and polyglutamic acid moiety having 21 of the polymerization number, to aspartic acid-1-adamantane methyl amide-4-(3'-ethynylcytidine) amide: Compound of general formula (III) wherein $R^1$=methyl group, $R^3$=trimethylene group, $R^4$=acetyl group, $R^7$ and $R^8$=hydrogen atom, $R^6$=1-adamantylmethyl group, p=q=1, i+n=21 and b=273 (Compound 15)

489 mg of a block copolymer of methoxy polyethylene glycol-polyglutamic acid prepared by the method described in the pamphlet of WO 2006/120914 A was dissolved in 10 mL of DMF. 600 mg of Compound 14 obtained in Synthesis Example 12, 192 μL of triethyl amine, 221 μL of DIPCI and 94.0 mg of HOBt were added thereto, and the reaction solution was stirred at 20° C. 19 hours. Furthermore, 53 μL of triethyl amine and 55 μL of DIPCI were added thereto, and the reaction solution was stirred for 4 hours, and then slowly dropped to a mixed solution of 10 mL of ethanol and 90 mL of diisopropyl ether. The reaction solution was stirred at room temperature for 1 hour. The deposit was taken by filtration and washed with ethanol/diisopropyl ether (1/9(v/v), 10 mL). The deposit was dissolved in 8 mL of DMF, slowly dropped to a mixed solution of 10 mL of ethanol and 90 mL of diisopropyl ether, and stirred at room temperature for 1 hour. The deposit was taken by filtration and washed with ethanol/diisopropyl ether (1/9(v/v), 4 mL). The deposit was dissolved in 10 mL of acetonitrile and 10 mL of water, and then added with ion exchange resin (DOWEX 50(H$^+$) manufactured by The Dow Chemical Company, 1 mL) and stirred, and the resin was taken by filtration and washed with acetonitrile/water (1/1(v/v), 10 mL). The obtained solution was distilled under reduced pressure to remove acetonitrile, and then freeze-dried, thereby to give 775 mg of Compound 15.

The content of the 3'-ethynylcytidine bonded to Compound 15 was analyzed in a similar manner to in Example 1 using HPLC (high performance liquid chromatography) after the hydrolysis and the content was calculated. The content of the 3'-ethynylcytidine bonded was 19.5% (w/w).

Calculation of the RMS radius was performed by Gaussian distribution analysis and static light scattering method using an aqueous solution (1 mg/mL) of Compound 15, and as results, the RMS radius was each 20 nm (volume weighting) and 13 nm. Accordingly, it was contemplated that Compound 15 formed a micelle in water.

Synthesis Example 13

Synthesis of phenylalanine phenylbutyl ester (Compound 16)

5.03 g of phenylalanine and 22.8 g of 4-phenyl-1-butanol were added to 17 mL of 1,4-dioxane, 17 mL of 4N—HCl/1,4-dioxane was added thereto, and the reaction solution was stirred at room temperature for 4 days. The reaction solution was filtered and the filtrate was added with 450 mL of diethyl ether, and stirred at room temperature for 1.5 hours. The deposit was taken by filtration, washed with 50 mL of diethyl ether, and then dried under vacuum, thereby to give 5.90 g of Compound 16.

$^1$H-NMR (400 MHz, CDCl$_3$, ppm): 1.44-1.55 (m, 4H), 2.53 (t, 2H), 3.31 (dd, 2H), 3.44 (dd, 2H), 4.05 (t, 2H), 4.44 (dd, 1H), 7.11-7.29 (m, 10H), 8.74 (br, 2H)

MS: m/z 298 (M+H)$^+$: 298 of calculated value as C19H$_{23}$NO$_2$ (M+H)$^+$

Synthesis Example 14

Synthesis of N-(tert-butoxycarbonyl)aspartic acid-1-phenylalanine-(4-phenylbutyl ester)amide-4-benzyl ester (Compound 17)

2.08 g of N-(tert-butoxycarbonyl)aspartic acid-4-benzyl ester and 2.18 g of Compound 16 obtained in Synthesis Example 13 were dissolved in 20 mL of DMF, and then 1.43 g of WSC hydrochloride and 0.943 g of HOBt were added thereto, and the reaction solution was stirred at room temperature overnight. The reaction solution was added with water, and extracted with ethyl acetate. The organic layer was washed with a saturated aqueous solution of sodium hydrogen carbonate, dried with magnesium sulfate, and then distilled under reduced pressure to remove ethyl acetate, and then dried under vacuum, thereby to give 1.18 g of Compound 17.

$^1$H-NMR (400 MHz, CDCl$_3$, ppm): 1.42 (s, 6H), 1.57-1.61 (m, 4H), 2.60 (t, 2H), 2.69 (dd, 1H), 3.02-3.08 (m, 3H), 4.04-4.13 (m, 2H), 4.52 (br, 1H), 4.78 (dd, 1H), 5.11 (d, 1H), 5.14 (d, 1H), 5.62 (br, 1H), 6.95 (br, 1H), 7.12-7.38 (m, 15H)

MS: m/z 625 (M+Na)$^+$: 625 of calculated value as C35H$_{42}$N$_2$O$_7$ (M+Na)$^+$ Synthesis Example 15

Synthesis of N-(tert-butoxycarbonyl)aspartic acid-1-phenylalanine-(4-phenylbutyl ester) amide (Compound 18)

1.18 g of Compound 17 obtained in Synthesis Example 14 was dissolved in 5 mL of ethyl acetate, and 0.118 g of 10% palladium carbon (50% moisture content) was added thereto. Then, the inside of the reaction system was substituted with hydrogen, and the reaction system was stirred at room temperature overnight. The 10% palladium carbon was filtered off, and washed with 20 mL of ethyl acetate. Then, the organic layers were combined, distilled under reduced pressure to remove ethyl acetate, and then dried under vacuum, thereby to give 1.18 g of Compound 18.

$^1$H-NMR (400 MHz, CDCl$_3$, ppm): 1.42 (s, 19H), 1.58 (m, 4H), 2.60 (t, 2H), 2.70 (dd, 1H), 2.98-3.09 (m, 3H), 4.03-4.12 (m, 2H), 4.52 (br, 1H), 4.79 (dd, 1H), 5.61 (d, 1H), 7.06-7.38 (m, 11H)

MS: m/z 535 (M+Na)$^+$: 535 of calculated value as C28H$_{36}$N$_2$O$_7$ (M+Na)$^+$ Synthesis Example 16

Synthesis of N-(tert-butoxycarbonyl)aspartic acid-1-phenylalanine-(4-phenylbutyl ester)-4-(3'-ethynylcytidine) amide (Compound 19)

200 mg of Compound 18 obtained in Synthesis Example 15, 87.0 mg of 3'-ethynylcytidine and 55.0 mg of HOBt were dissolved in 2 mL of DMF, and then the reaction solution was frozen and degassed. Then, 70.6 mg of WSC hydrochloride was added thereto, and the reaction solution was stirred at 20° C. for 6 hours. Subsequently, 35.3 mg of WSC hydrochloride was added thereto, and the reaction solution was stirred at 20° C. for 2 hours. The reaction solution was added with water, and extracted with ethyl acetate. The organic layer was washed with a saturated aqueous solution of ammonium chloride and a saturated aqueous solution of sodium hydrogen carbonate, dried with magnesium sulfate, and then distilled under reduced pressure to remove ethyl acetate, and the obtained oily substance was purified with silica gel column chromatography ($CHCl_3$/n-Hexane), to give 155 mg of Compound 19.

MS: m/z 784 $(M+Na)^+$: 784 of calculated value as $C39H_{47}N_5O_{11}$ $(M+Na)^+$ Synthesis Example 17

Synthesis of aspartic acid-1-phenylalanine-(4-phenylbutyl ester)-4-(3'-ethynylcytidine) amide (Compound 20)

155 mg of Compound 19 obtained in Synthesis Example 16 was dissolved in 1 mL of ethyl acetate, and then 510 μL of 4N—HCl/AcOEt was added thereto, and the reaction solution was stirred at room temperature for 1 hour. After completion of the reaction, the reaction solution was distilled under reduced pressure to remove ethyl acetate, and then dried under vacuum, thereby to give 105 mg of Compound 20.

$^1$H-NMR (400 MHz, DMSO-$d_6$, ppm): 1.51 (s, 4H), 2.22-2.24 (m, 3H), 2.78-3.07 (m, 4H), 3.31-4.18 (m, 6H), 4.50 (s, 1H), 5.83 (d, 1H), 5.89 (d, 1H), 6.28 (br, 1H), 7.19-7.26 (m, 11H), 8.34 (br, 2H), 8.94 (s, 1H), 9.09 (br, 2H), 10.1 (br, 1H), 11.3 (br, 1H)

MS: m/z 684 $(M+Na)^+$: 684 of calculated value as $C34H_{39}N_5O_9$ $(M+Na)^+$

Example 4

Synthesis of amide-bonded body of block copolymer including methoxy polyethylene-glycol structural moiety having 12,000 of the molecular weight and polyglutamic acid moiety having 21 of the polymerization number, to aspartic acid-1-phenylalanine-(4-phenylbutyl ester)-4-(3'-ethynylcytidine)amide: Compound of general formula (III) wherein $R^1$=methyl group, $R^3$=trimethylene group, $R^4$=acetyl group, $R^7$ and $R^8$=hydrogen atom, $R^6$=1-phenylalanine-4-phenylbutyl ester group, p=q=1, i+n=21 and b=273 (Compound 21)

66 mg of a block copolymer of methoxy polyethylene glycol-polyglutamic acid prepared by the method described in the pamphlet of WO 2006/120914 A was dissolved in 2 mL of DMF. 100 mg of Compound 20 obtained in Synthesis Example 17, 23 μL of triethyl amine, 39 μL of DIPCI and 13 mg of HOBt were added thereto, and the reaction solution was stirred at 20° C. for 4 hours. Furthermore, 19 μL of triethyl amine and 20 μL of DIPCI were added thereto, and the reaction solution was stirred for 16 hours, and then slowly dropped to a mixed solution of 4 mL of ethanol and 36 mL of diisopropyl ether. The reaction solution was stirred at room temperature for 0.5 hours. The deposit was taken by filtration and washed with ethanol/diisopropyl ether (1/9(v/v), 4 mL). The deposit was dissolved in a small amount of DMF, and slowly dropped to a mixed solution of 4 mL of ethyl acetate and 24 mL of diisopropyl ether, and stirred at room temperature for 3 hours. The deposit was taken by filtration and washed with ethyl acetate/diisopropyl ether (1/6(v/v), 4 mL).

The deposit was dissolved in 2.5 mL of acetonitrile and 2.5 mL of water, and then added with ion exchange resin (DOWEX 50($H^+$) manufactured by The Dow Chemical Company, 0.5 mL) and stirred, and the resin was taken by filtration and washed with acetonitrile/water (1/1(v/v), 3 mL). The obtained solution was distilled under reduced pressure to remove acetonitrile, and then freeze-dried, thereby to give 36.5 mg of Compound 21.

The content of the 3'-ethynylcytidine bonded to Compound 21 was analyzed in a similar manner to in Example 1 using HPLC (high performance liquid chromatography) after the hydrolysis and the content was calculated. The content of the 3'-ethynylcytidine bonded was 22.5% (w/w).

Calculation of the RMS radius using an aqueous solution (1 mg/mL) of Compound 21 was performed by Gaussian distribution analysis and static light scattering method, and as results, the RMS radius was each 41 nm (volume weighting) and 40 nm. Accordingly, it was contemplated that Compound 21 formed a micelle in water.

Example 5

Synthesis of amide-bonded body of block copolymer including two methoxy polyethylene glycol moieties having 5,000 of the molecular weight and polyglutamic acid moiety having 21 of the polymerization number, to aspartic acid-1-adamantane methyl amide-4-(3'-ethynylcytidine)amide: Compound of general formula (III) wherein $R^1$=methyl group, $R^3$=linking group of formula (V), r=3, $R^4$=acetyl group, $R^7$ and $R^8$=hydrogen atom, $R^6$=1-adamantylmethyl group, i+n=21 and b=114 (Compound 22)

413 mg of (methoxy polyethylene glycol)$_2$-polyglutamic acid block copolymer, which was prepared from (methoxy polyethylene glycol)$_2$-amine (SUNBRIGHT GL2-100PA; manufactured by NOF CORPORATION) by applying the method described in the pamphlet of WO 2006/120914 A, was dissolved in 8.3 mL of DMF. Then, 570 mg of Compound 14 obtained in Synthesis Example 12, 183 μL of triethyl amine, 210 μL of DIPCI and 89 mg of HOBt were added thereto, and the reaction solution was stirred at 20° C. for 17 hours. Furthermore, 51 μL of triethyl amine and 105 μL of DIPCI were added thereto, and the reaction solution was stirred for 3 hours, and then slowly dropped to a mixed solution of 10 mL of ethanol and 90 mL of diisopropyl ether. The reaction solution was stirred at room temperature for 0.5 hours. The deposit was taken by filtration and washed with ethanol/diisopropyl ether (1/9(v/v), 10 mL). The deposit was dissolved in 8 mL of DMF, slowly dropped to a mixed solution of 10 mL of ethanol and 90 mL of diisopropyl ether, and stirred at room temperature for 0.5 hours. The deposit was taken by filtration and washed with ethanol/diisopropyl ether (1/9(v/v), 4 mL). The deposit was dissolved in 35 mL of acetonitrile and 17.5 mL of water, added with ion exchange resin (DOWEX 50($H^+$) manufactured by The Dow Chemical Company, 5 mL) and stirred, and the resin was taken by filtration and washed with acetonitrile/water (1/1(v/v), 10 mL×2). The obtained solution was distilled under reduced pressure to remove acetonitrile, and then freeze-dried, thereby to give 685 mg of Compound 22.

The content of the 3'-ethynylcytidine bonded to Compound 22 was analyzed in a similar manner to in Example 1 using HPLC (high performance liquid chromatography) after the hydrolysis and the content was calculated. The content of the 3'-ethynylcytidine bonded was 20.2% (w/w).

Calculation of the RMS radius using an aqueous solution (1 mg/mL) of Compound 22 was performed by Gaussian distribution analysis and static light scattering method, and as results, the RMS radius was each 14 nm (volume weighting) and 8 nm. Accordingly, it was contemplated that Compound 22 formed a micelle in water.

Test Example 1

Medicament Release of 3'-ethynylcytidine polymer Derivative in the Absence of Enzyme Compound 5, Compound 10, Compound 15, Compound 21 and Compound 22, and PEG-Glu-ECyd in which 3'-ethynylcytidine derivative is bonded to a polyethylene glycol-polyglutamic acid block copolymer, and PEG-Glu-(ECyd, PheOBzl) in which 3'-ethynylcytidine and phenylalanine benzyl ester are bonded to a polyethylene glycol-polyglutamic acid block copolymer, which were manufactured by the method described in the pamphlet of WO 2006/120914 A as the comparative compounds, were dissolved in PBS solution (phosphate buffered saline; pH 7.4) at 1 mg/mL of the concentration, respectively, and incubated at 37° C. The 3'-ethynylcytidine released from each polymer derivative was quantified using HPLC. The ratio to the total amount of the medicament in the polymer derivative found out from the quantified value and the content of the medicament of the polymer derivative are indicated in FIGS. 1 to 3.

Figure 2:
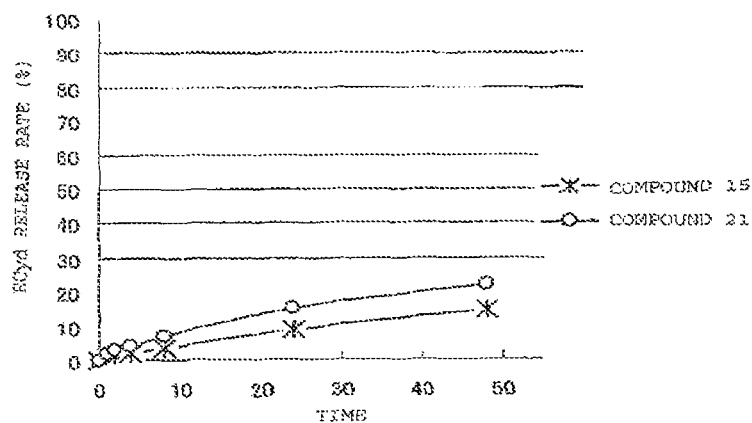
FIG. 2 represents the ratio of the release amount of 3'-ethynylcytidine (ECyd) for Compound 15 and Compound 21 of Examples at 37° C. in a PBS solution (phosphate buffered saline, pH 7.4) with respect to the total bonding amount.
Figure 3:
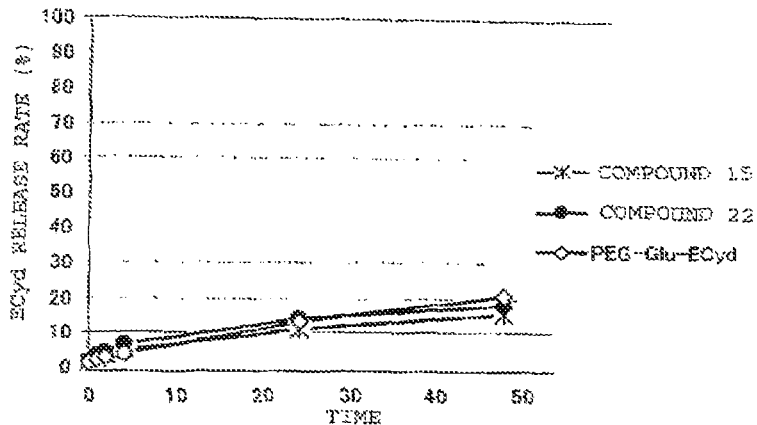
FIG. 3 represents the ratio of the release amount of 3'-ethynylcytidine (ECyd) for Compound 15 and Compound 22 of Examples, and the comparative compounds (PEG-Glu-ECyd) at 37° C. in a PBS solution (phosphate buffered saline, pH 7.4) with respect to the total bonding amount.

As indicated from FIGS. 1 to 3, it was possible for the polymer derivative of the present invention (Compound 5, Compound 10, Compound 15, Compound 21 and Compound 22) to release 3'-ethynylcytidine despite the absence of a hydrolysis enzyme, and to greatly change the release rate by means of the substituent of $R^6$ that is bonded to the aspartic acid, and the release rate was equal to or more than that of the comparative compounds. Particularly, it was possible for Compound 5 and Compound 10 to release 3'-ethynylcytidine sufficiently, more rapidly than PEG-Glu-ECyd. On the other hand, it is not possible for the comparative compounds to increase the release rate since they do not have succinic acid monoamide structural moiety in the block copolymer. These results show that the polymer-bonded body of the present invention is excellent in regulation ability of the release rate of the medicament.

Test Example 2

Anti-Tumor Activity Test of 3'-ethynylcytidine Derivative

The human lung cancer LC-11-JCK which had been subcultured under the skin of a rat was made to a block of about 2 mm square, and transplanted subcutaneously into the dorsal part of F344 nude rat using an over-needle catheter. From day 13 after the tumor transplant, the polymer derivative of the present invention (Compound 5, Compound 10) was administered intravenously single time in the dose listed in Table 1. In addition, the control drug (3'-ethynylcytidine; ECyd) was administered subcutaneously by infusion over 24 hours using Alzet pump. Meanwhile, each compound was used as dissolved in 5% glucose solution. The administration was performed such that the dose when the change of the body weight was about 10% of the maximum decrease rate was taken as the maximum dose.

The tumor volume was measured on the start day of the administration and on day 23 after the administration start with vernier calipers for the major axis (L mm) and minor axis (W mm) of the tumor, and the tumor volume was calculated from $(L \times W^2)/2$, and the relative ratio of the tumor volume with respect to the tumor volume of the no-treatment group (control) was listed in Table 1.

TABLE 1

| Medicament | Dose (In conversion to 3'-ethynylcytidine) (mg/Kg) | Relative ratio of tumor volume |
|---|---|---|
| No-treatment | 0 | 100.0 |
| Compound 5 | 12 | 29.3 |
|  | 6 | 44.9 |
| Compound 10 | 12 | 26.4 |
|  | 6 | 46.7 |
| Control drug | 6 | 49.4 |

From these results, Compound 5 and Compound 10, i.e., the polymer derivatives of the present invention, exhibited strong anti-tumor effects in the maximum dose when the change of the body weight was about 10% or less of the maximum decrease rate in comparison to 3'-ethynylcytidine as the control drug, and the polymer derivatives of the present invention exhibited equal effects in the half of the amount to those by the maximum dose of the control drug.

The invention claimed is:

1. A polymer derivative of a cytidine metabolic antagonist bonding a substituent represented by the general formula (I) or the general formula (II) to a side-chain carboxy group of a block copolymer of a polyethylene-glycol structural moiety and a polymer having 10 or more carboxy groups

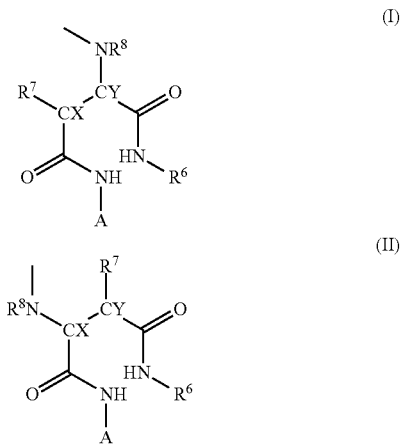

[wherein, $R^7$ and $R^8$ each independently represent a hydrogen atom or an optionally substituted (C1-C6)alkyl group, $R^6$ represents a hydrogen atom, an optionally substituted (C1-C40)alkyl group, an optionally substituted (C1-C40)aralkyl group, an optionally substituted aromatic group, an amino acid residue in which the carboxy group is protected, or an optionally substituted sugar residue, CX—CY represents CH—CH or C═C (double bond), and A represents the residue of the cytidine metabolic antagonist except the amino group at the position 4].

2. The polymer derivative of a cytidine metabolic antagonist according to claim 1, wherein the polymer having 10 or more carboxy groups is polyamino acid or a derivative thereof.

3. The polymer derivative of a cytidine metabolic antagonist according to claim 2, wherein the polyamino acid is polyglutamic acid.

4. The polymer derivative of a cytidine metabolic antagonist according to claim 1, wherein the polymer derivative of a cytidine metabolic antagonist is a compound represented by the general formula (III)

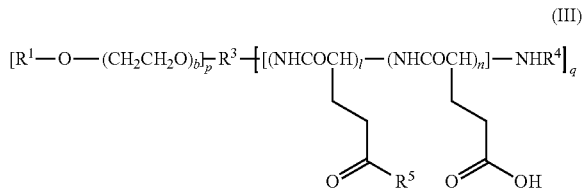

(III)

[wherein, $R^1$ represents a hydrogen atom or a (C1-C6)alkyl group, $R^3$ represents a linking group, $R^4$ represents a hydrogen atom or a (C1-C6)acyl group, $R^5$ represents a substituent represented by the general formula (I) or the general formula (II)

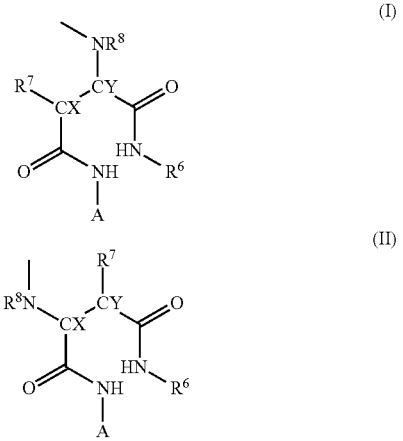

(I)

(II)

[wherein, $R^6$, $R^7$ and $R^8$, CX—CY and A are as defined in claim 1, ], b represents an integer of 5 to 11,500, p and q each independently represent an integer of 1 to 3, i represents an integer of 5 to 200, n represents an integer of 0 to 200, and i+n represents an integer of 10 to 300].

5. The polymer derivative of a cytidine metabolic antagonist according to claim 4, wherein $R^1$ is a (C1-C3)alkyl group, $R^3$ is a linking group represented by the formula (IV), (V) or (VI)

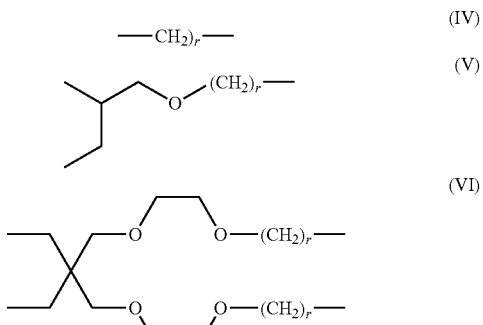

[wherein, r represents an integer of 1 to 6], $R^4$ is a (C1-C3) acyl group, b is an integer of 100 to 300, p and q is each 1 or 2 depending on $R^3$, i is an integer of 5 to 90, n is an integer of 0 to 90, and i+n is an integer of 10 to 100.

6. The polymer derivative of a cytidine metabolic antagonist according to claim 5, wherein $R^1$ is a methyl group, $R^3$ is a trimethylene group, $R^4$ is an acetyl group, both of $R^7$ and $R^8$ in $R^5$ are a hydrogen atom, and CX—CY is CH—CH.

7. The polymer derivative of a cytidine metabolic antagonist according to claim 4, wherein the cytidine metabolic antagonist is gemcitabine, 5'-deoxy-5-fluorocytidine, cytarabine or 3'-ethynylcytidine.

8. An anticancer agent containing the polymer derivative of a cytidine metabolic antagonist according to claim 4 as an active ingredient.

9. An anti-virus agent containing the polymer derivative of a cytidine metabolic antagonist according to claim 4 as an active ingredient.

10. The polymer derivative of a cytidine metabolic antagonist according to claim 4, wherein the polymer derivative of a cytidine metabolic antagonist forms a micelle in water.

* * * * *